(12) United States Patent
Hunt et al.

(10) Patent No.: US 8,430,099 B2
(45) Date of Patent: Apr. 30, 2013

(54) APPARATUS, SYSTEMS AND METHOD FOR COLLECTING AND RECLAIMING ANAESTHETIC AGENTS AND FOR REMOVING NITROUS OXIDE FROM EXHAUST GASES

(75) Inventors: Barry W. Hunt, Kitchener (CA); Todd Eric Jarrett, Burlington (CA); Damian Ross Thorne, Kitchener (CA); Katrina Marie Ahchong, Toronto (CA); Dean Paul Carr, Kitchener (CA); Cesar Laurentino Martinez Vazquez, Cambridge (CA)

(73) Assignee: CLass 1 Inc., Cambridge, Ontario (CA)

( * ) Notice: Subject to any disclaimer, the term of this patent is extended or adjusted under 35 U.S.C. 154(b) by 0 days.

(21) Appl. No.: 13/231,718

(22) Filed: Sep. 13, 2011

(65) Prior Publication Data

US 2012/0000549 A1 Jan. 5, 2012

Related U.S. Application Data

(62) Division of application No. 13/256,367, filed as application No. PCT/CA2011/000181 on Feb. 17, 2011.

(60) Provisional application No. 61/306,915, filed on Feb. 22, 2010, provisional application No. 61/368,608, filed on Jul. 28, 2010.

(51) Int. Cl.
*A61M 16/01* (2006.01)

(52) U.S. Cl.
USPC .................. 128/205.12; 128/205.27; 137/2; 137/467.5; 137/487.5

(58) Field of Classification Search ............... 137/467.5, 137/487.5, 2; 128/205.15, 205.27, 205.12
See application file for complete search history.

(56) References Cited

U.S. PATENT DOCUMENTS

| 1,175,006 | A | 3/1916 | Montgomery |
| 2,667,397 | A | 1/1954 | Hallisey |
| 3,140,931 | A | 7/1964 | McRobbie |

(Continued)

FOREIGN PATENT DOCUMENTS

| DE | 4208521 | 9/1993 |
| WO | 2011026230 | 3/2011 |

OTHER PUBLICATIONS

International Searching Authority, Written Opinion and International Search Report, May 25, 2011.

(Continued)

*Primary Examiner* — William McCalister
(74) *Attorney, Agent, or Firm* — Bereskin & Parr LLP

(57) ABSTRACT

A system for collecting an anaesthetic agent, having at least one anaesthetic gas scavenging system (AGSS) for receiving exhaust gas from a plurality of sources, the exhaust gas including the anaesthetic agent to be collected, each AGSS comprising at least one power source for providing suction of the exhaust gas from the plurality of sources under negative pressure, and a central collection system for receiving the exhaust gas, the central collection system comprising at least one collector for collecting the anaesthetic agent from the exhaust gas, wherein the at least one collector is configured to adsorb the anaesthetic agent from the exhaust gas. The central collection system may be configured to received the exhaust gases from the at least one AGSS, with the central collection system being located downstream of the at least one AGSS.

17 Claims, 14 Drawing Sheets

U.S. PATENT DOCUMENTS

| | | |
|---|---|---|
| 3,469,011 A | 9/1969 | Terrell |
| 3,527,813 A | 9/1970 | Terrell |
| 3,535,388 A | 10/1970 | Terrell |
| 3,535,425 A | 10/1970 | Terrell |
| 3,592,191 A | 7/1971 | Jackson |
| 3,707,066 A | 12/1972 | Carne et al. |
| 3,721,097 A | 3/1973 | Briley et al. |
| 3,729,902 A | 5/1973 | Ventriglio et al. |
| 3,791,403 A | 2/1974 | Folkerth |
| 3,853,507 A | 12/1974 | Monroe et al. |
| 3,861,412 A * | 1/1975 | Fleischmann ............ 137/83 |
| 3,867,936 A | 2/1975 | Kelley |
| 3,941,573 A | 3/1976 | Chapel |
| 4,026,284 A | 5/1977 | Boehringer |
| 4,082,092 A | 4/1978 | Foster |
| 4,109,651 A | 8/1978 | Steigerwald |
| 4,188,946 A | 2/1980 | Watson et al. |
| 4,222,750 A | 9/1980 | Gauthier et al. |
| 4,259,303 A | 3/1981 | Nakaji et al. |
| 4,350,662 A | 9/1982 | Dowgul et al. |
| 4,382,440 A | 5/1983 | Kapp et al. |
| 4,534,346 A | 8/1985 | Schlaechter |
| 4,668,261 A | 5/1987 | Chatzipetros et al. |
| 4,726,817 A | 2/1988 | Roger |
| 4,737,164 A | 4/1988 | Sarkkinen |
| 4,755,201 A | 7/1988 | Eschwey et al. |
| 4,799,374 A | 1/1989 | Bossart et al. |
| 4,810,265 A | 3/1989 | Lagree et al. |
| 4,903,693 A | 2/1990 | Yasue |
| 4,905,685 A | 3/1990 | Olsson et al. |
| 5,044,361 A | 9/1991 | Werner et al. |
| 5,044,363 A | 9/1991 | Burkhart |
| 5,110,328 A | 5/1992 | Yokota et al. |
| 5,171,553 A | 12/1992 | Li et al. |
| 5,231,980 A | 8/1993 | Filipovic et al. |
| 5,308,457 A | 5/1994 | Dalla Betta et al. |
| 5,388,637 A | 2/1995 | Jones et al. |
| 5,515,845 A | 5/1996 | Filipovic et al. |
| 5,520,169 A | 5/1996 | Georgieff et al. |
| 5,575,832 A | 11/1996 | Boyd |
| 5,626,035 A | 5/1997 | Pozvonkov |
| 5,692,497 A | 12/1997 | Schnitzer et al. |
| 5,827,355 A | 10/1998 | Wilson et al. |
| 5,912,424 A | 6/1999 | Judkins et al. |
| 5,917,135 A | 6/1999 | Michaels et al. |
| 6,131,571 A * | 10/2000 | Lampotang et al. ..... 128/204.21 |
| 6,134,914 A | 10/2000 | Eschwey et al. |
| 6,347,627 B1 | 2/2002 | Frankie et al. |
| 6,364,936 B1 | 4/2002 | Rood et al. |
| 6,405,539 B1 | 6/2002 | Stach et al. |
| 7,066,985 B2 | 6/2006 | Deane et al. |
| 7,235,222 B2 | 6/2007 | Hotta et al. |
| 7,246,621 B2 | 7/2007 | McNeirney |
| 2005/0155380 A1 | 7/2005 | Rock |
| 2006/0254586 A1 | 11/2006 | Berry et al. |
| 2006/0254589 A1 | 11/2006 | Berry et al. |
| 2012/0222556 A1 | 9/2012 | Filipovic et al. |

OTHER PUBLICATIONS

CIPO Examiner's Report, Mar. 22, 2012, Canadian Patent Application Serial No. 2,763,021.

* cited by examiner

APPARATUS, SYSTEMS AND METHOD FOR COLLECTING AND RECLAIMING ANAESTHETIC AGENTS AND FOR REMOVING NITROUS OXIDE FROM EXHAUST GASES

RELATED APPLICATIONS

This application is a divisional of U.S. patent application Ser. No. 13/256,367, which entered national phase on Sep. 13, 2011 and is entitled "Apparatus, Systems and Methods for Collecting and Reclaiming Anaesthetic Agents and for Removing Nitrous Oxide from Exhaust Gases", which is a National Phase Entry of PCT International Application No. PCT/CA2011/000181 filed on Feb. 17, 2011 and entitled "Apparatus, Systems and Methods for Collecting and Reclaiming Anaesthetic Agents and for Removing Nitrous Oxide from Exhaust Gases", which claims the benefit of U.S. Provisional Patent Application Ser. No. 61/306,915 filed on Feb. 22, 2010 and entitled "Apparatus, Systems and Methods for Collecting and Reclaiming Anaesthetic Agents", and also claims the benefit of U.S. Provisional Patent Application Ser. No. 61/368,608 filed on Jul. 28, 2010 and entitled "Apparatus, Systems and Methods for Collecting and Reclaiming Anaesthetic Agents and for Removing Nitrous Oxide from Exhaust Gases", the entire contents of all of which are hereby incorporated by reference herein for all purposes.

TECHNICAL FIELD

Embodiments described herein relate to apparatus, systems and methods for collecting and/or reclaiming anaesthetic agents, and in particular, for reclaiming halogenated drugs from exhaust gases such as waste air expelled by patients in operating rooms, as well as for removing other substances from exhaust gases such as nitrous oxide, oxygen, and biological substances.

INTRODUCTION

Numerous devices are known for collecting and/or reclaiming anaesthetic agents such as halogenated drugs or nitrous oxide.

For example U.S. Pat. No. 3,592,191 (Jackson) discloses a method and apparatus for recovering exhausted anaesthetic agents. Recovery is effected by collecting the exhausted gas and removing the water vapor either by condensation or with a hygroscopic material. The anesthetic agent is then extracted from the dried gas by a cryogenic process in which the vapors in the anesthetic agent are condensed to a liquid phase or by an absorbent material, which is processed later to remove the agent. When employing the condensing process, the anesthetic condensate is collected and may be readmitted directly into the anesthetic system.

U.S. Pat. No. 7,235,222 (Hotta et al.) discloses a process and an apparatus for treating a waste anesthetic gas containing a volatile anesthetic and nitrous oxide discharged from an operating room by introducing the gas into an adsorbing cylinder filled with an adsorbent, where the volatile anesthetic contained in the waste anesthetic gas is adsorbed and thereby removed, and successively introducing the gas into a catalyst layer filled with a nitrous oxide decomposition catalyst, where nitrous oxide is decomposed into nitrogen and oxygen.

U.S. Patent Application Publication Number 2005/0155380 (Rock) discloses devices for the recovery of volatile, organic anesthetic agents from waste anesthesia gas. The device recovers the anesthetic agents by selectively condensing the agents in a cooling chamber and storing the condensed agents in a pressurized storage chamber.

U.S. Patent Application Publication Number 2006/0254586 (Berry et al.) discloses a method and system for removal of nitrous oxide and volatile halocarbon gas components from waste anesthetic gases using a low-flow scavenging or reclamation system that preferably includes an intelligent waste anesthetic gas collection unit fluidly coupled between each individual anesthetic machine and the waste gas evacuation manifold. Through a system including a collection chamber, a pressure detector, and an exhaust valve which is actuated based on the detected pressure in the collection chamber, the waste anesthetic gas collection unit allows flow to the waste suction manifold only in the presence of waste gas and interrupts all flow into the suction manifold when no waste gas is present.

U.S. Patent Application Publication Number 2006/0254589 (Berry et al.) discloses a method and apparatus for recovering and separating anesthetic gas components from waste anesthetic gases to be purged from a healthcare facility. Prior to a condensation step, a compressor is used to increase the waste anesthetic gas pressure in order to facilitate condensation of anesthetic gas components at higher temperatures and in greater amounts than through condensation at lower pressures. Condensing the anesthetic gas components from the compressed waste anesthetic gas stream is then achieved using conventional condensation systems, which remove anesthetic gases as either liquid condensates or solid frosts. Some embodiments may be used with existing high-flow scavenging or reclamation systems but are more preferably used with low-flow scavenging or reclamation systems, which employ intelligent waste anesthetic gas collection units to minimize the ingress of atmospheric gas when no waste anesthetic gas is to be purged from the healthcare facility.

In spite of these known devices, a need for apparatus, systems and methods of collecting and/or reclaiming anaesthetic agents such as halogenated drugs or nitrous oxide has been recognized.

BRIEF DESCRIPTION OF THE DRAWINGS

The drawings included herewith are for illustrating various examples of methods and apparatus of the present specification and are not intended to limit the scope of what is taught in any way. In the drawings.

DETAILED DESCRIPTION

Figure 1:
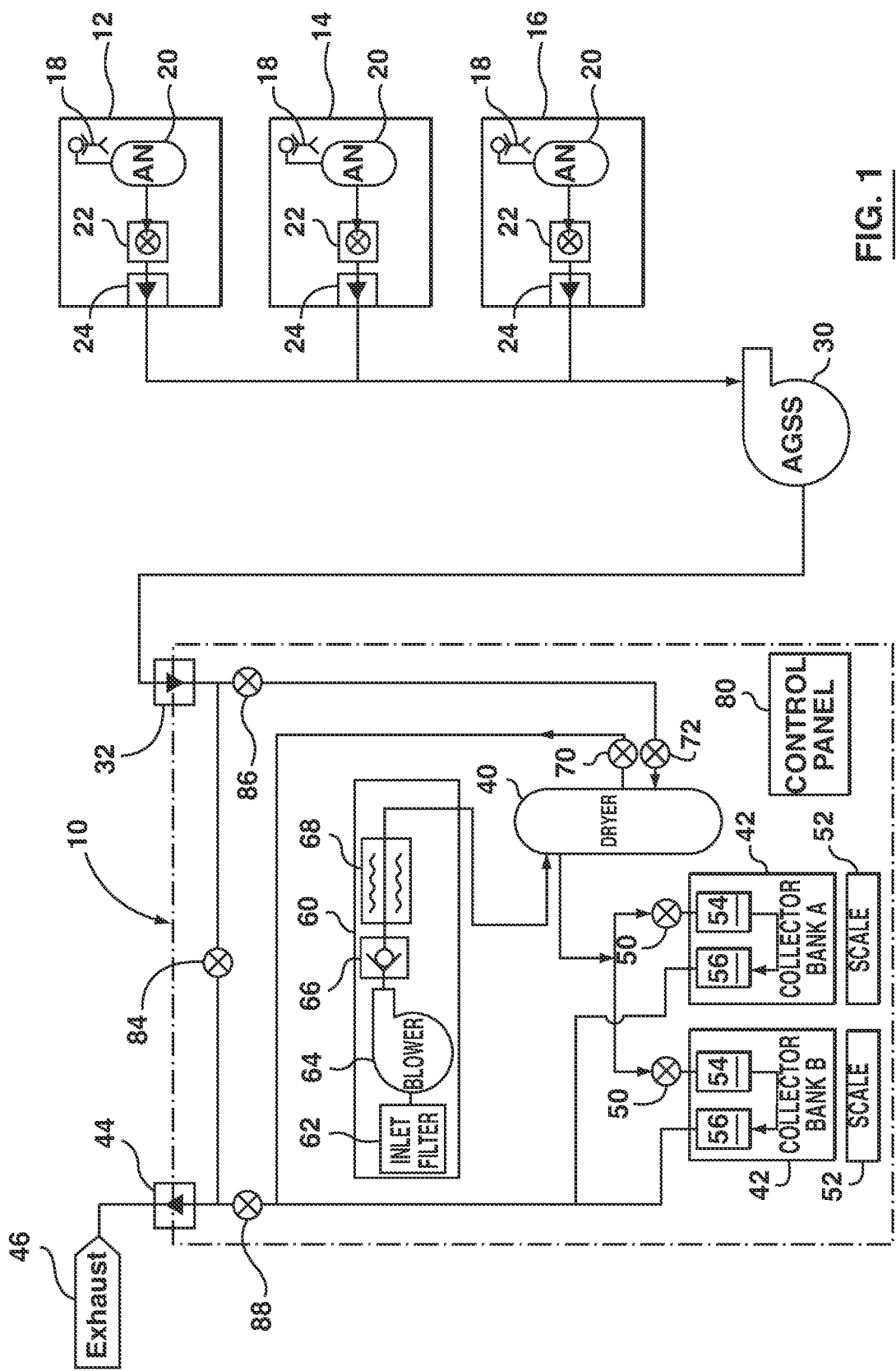
FIG. 1 is a schematic representation of a collection system for collecting anaesthetic agents according to one embodiment.

Referring to FIG. 1, illustrated therein is a collection system 10 for collecting or reclaiming anesthetic agents such as halogenated drugs or nitrous oxide from one or more sources of exhaust gas according to some embodiments. The collection system 10 may be installed in a healthcare facility such as a hospital and may be centrally located such that it is in fluid communication with one or more sources of exhaust gas, such as one or more operating rooms 12, 14, and 16.

Furthermore, the collection system 10 may be remotely located relative to the operating rooms 12, 14, 16 and other sources of exhaust gas. For example, the collection system 10 may be located within the hospital at a location that is both central and remote relative to the individual operating rooms 12, 14, 16 while remaining in fluid communication with the operating rooms 12, 14, 16, (e.g. via piping, ducting or other mediums for transporting liquids or gases, collectively referred to as "piping" herein).

The operating rooms 12, 14, 16 may be the source of one or more exhaust gases. For example, each operating room 12, 14, 16 may have an anaesthetic machine 20 that can be connected to one or more patients 18 for administering one or more anaesthetic agents (such as halogenated drugs, nitrous oxide, etc.) during or in association with a medical procedure.

In some cases, the anaesthetic machine 20 may also collect exhaust gases from the patient 18 and direct those exhaust gases to the collection system 10, for example, through an exhaust port 24 in the operating room. In some embodiments, a conservation valve 22 may be located between the anaesthetic machine 20 and the exhaust port 24 as will be described below.

In some embodiments, the exhaust gases may come from other sources, such as an outpatient clinic, a surgery clinic, a doctor's office, an oral surgery clinic, a veterinary clinic, or other types of healthcare facilities.

As shown, an Anaesthetic Gas Scavenging System 30 ("AGSS"), also known as a Waste Anaesthetic Gas Disposal ("WAGD"), may be connected to the operating rooms 12, 14, 16 and the collection system 10. As shown, the AGSS 30 may be located between the operating rooms 12, 14, 16 and the collection system 10.

Generally, the AGSS 30 draws exhaust gases from the operating rooms 12, 14, 16 or another source, and directs these exhaust gases to the collection system 10. For example, the AGSS 30 may include a power source such as a vacuum pump, blower, or fan connected to the exhaust ports 24 of the operating rooms 12, 14, and 16 through piping. In some instances, the power source may be connected to an inlet port 32 of the collection system 10 through piping.

In some embodiments, the AGSS 30 may include two or more power sources connected in parallel. Having an additional power source may provide a back-up in case one power source stops operating (e.g. breaks down or needs maintenance), which may improve system redundancy. Additional power sources may also increase the suction, for example, when the AGSS 30 is connected to larger systems (e.g. a greater number of operating rooms). Furthermore, in some embodiments there may be more than one AGSS 30, which may be connected in parallel, for example, to provide redundancy.

Generally, the collection system 10 includes one or more collectors 42 for collecting and removing anesthetic agents from the exhaust gas. The collection system 10 may also include a dryer 40 for removing moisture from the exhaust gas, and may include a dryer regeneration module 60 operatively coupled to the dryer 40 as will be described below.

The collection system 10 may also include a controller 80 for controlling various subcomponents of the collection system 10 such as the collectors 42, the dryer 40 and the dryer regeneration module 60 as will be described below.

Under normal operating conditions, exhaust gases entering the collection system 10 typically pass through the dryer 40 first, and then through the collector 42. Accordingly, the dryer 40 and the collector 42 may be in fluid communication with each other.

After flowing through the dryer 40 and the collector 42, the exhaust gas may exit the collection system 10 at an outlet port 44, which may be coupled to an exhaust 46 that vents to atmosphere outside of a medical facility.

As shown, the dryer 40 is in fluid communication with the inlet port 32 and receives exhaust gas from the AGSS 30. Often, the exhaust gas collected from the operating rooms 12, 14, and 16 may include moisture entrained in the gas flow, which may adversely affect the amount of anesthetic agent collected by the collectors 42. For example, moisture may be exhaled by the patients 18 in the operating rooms 12, 14, 16 during medical procedures.

The dryer 40 helps to remove this moisture from the exhaust gas. For example, the dryer 40 may include desiccant material such as activated alumina, or may use other methods of drying air, such as condensation or membrane dryers, as will be described below.

The dryer 40 may be any suitable shape and size. For example, the dryer 40 may be a tower having an inlet at the bottom of the tower and an outlet at the top of the tower. In some cases, the size and shape of the tower may be determined according to the amount of moisture to be removed.

In one example, the dryer 40 may include approximately 2.5 kilograms of alumina desiccant for each operating room (e.g. operating rooms 12, 14, 16), which may allow the dryer 40 to continuously dehumidify exhaust gases from a typical patient for approximately eight hours. For example, in the illustrated embodiment, there are three operating rooms 12, 14, 16, and the dryer 40 may include at least 7.5 kilograms of alumina desiccant.

In some embodiments, more activated alumina may be provided in the dryer 40 so as to provide a buffer. For example, in the illustrated embodiment, approximately 10 kilograms of activated alumina may be provided in the dryer 40. The dryer 40 may also include more desiccant so as to provide a longer operating time (e.g. sixteen hours of continuous operation).

After flowing through the dryer 40, the dryer 40 outputs a dehumidified exhaust gas, which is then received by one or more collectors 42. In the illustrated embodiment, the collectors 42 adsorb anaesthetic agents from the exhaust gas. For example, the collectors 42 may include hollow vessels containing adsorbent material made from hydrophobic molecular sieves as generally described in U.S. Pat. No. 5,231,980 (Filipovic). The hydrophobic molecular sieves may be of the high silica zeolite type. According to Filipovic, such adsorbent materials have pore diameters large enough to permit molecules of halogenated drugs to pass therethrough and be selectively adsorbed in large internal cavities of the crystal framework, whereby halogenated drugs may be removed.

While the embodiment described above refers to a hydrophobic molecular sieve for collecting and reclaiming halogenated drugs, the collector 42 may collect anaesthetic agents using different materials or methods. For example, the collector 42 may utilize other adsorbent materials such as other types of molecular sieves or activated charcoal to collect and reclaim halogenated drugs. In some cases the collector 42 could use a cryogenic collector.

In normal operation, the exhaust gas passes through the collector 42 even when the collector is saturated or cannot remove anaesthetic agents from the exhaust gas flow. However, once the collector is full, the flow of exhaust gases may be diverted from the collector 42 that is full, and the anaesthetic agents may be recovered from that particular collector 42 for later reuse.

For example, when using the hydrophobic molecular sieve described by Filipovic, the exhaust gases may pass through a bed of adsorbent material until the material in the sieve is saturated to the extent that breakthrough of the hydrocarbons is determined (e.g. halogenated hydrocarbons are detected at the outlet of the collector). Next, the adsorbent material with the adsorbed phase of halogenated hydrocarbons may be removed from the system and regenerated by exposing the saturated material to an inert purging gas stream under conditions which desorb the halogenated hydrocarbons from the adsorbent material into the purging gas stream. The halogenated hydrocarbons may then be removed from the purging gas stream and purified to a desired level of purity for reuse of the recovered halogenated hydrocarbons.

In some embodiments, a third party may remove the anaesthetic agents (e.g. halogenated hydrocarbons) from the collector 42.

In some embodiment, after recovering the anaesthetic agents from the collector 42, the collector 42 may be reinstalled in the system 10. Accordingly, the collector 42 may be reused multiple times.

When recovering anaesthetic agents from the collector 42 it may be desirable to keep the system 10 operational so as to provide continuous collection of anaesthetic agents. Accordingly, the system 10 may include a plurality of collectors 42 (e.g. collector bank "A" and collector bank "B") connected together in parallel so that at least one collector 42 remains operational while one or more other collectors 42 are being processed to remove the captured anaesthetic agents, for example.

When there is a plurality of collectors 42 connected in parallel, the inlet of each collector 42 may include a valve 50 for selectively opening and closing the flow of exhaust gases into the respective collector 42 from the dryer 40. This valve 50 may be closed when removing the respective collector 42 from the system 10, for example, when recovering anaesthetic agents from each respective collector 42. At the same time, other collectors 42 may have open valves 50 such that dehumidified exhaust gases are permitted to flow into those other collectors. Accordingly, the collection system 10 may remain operational while some of the collectors 42 are being processed.

The collection system 10 may also include a sensor 52 for measuring an amount of anaesthetic agent collected and for detecting when one of the collectors 42 is full, for example, so that anaesthetic agents can be reclaimed, for example, by removing/exchanging the collector 42 from the system 10. In some embodiments, the sensor 52 may be a weight scale that measures the weight of the collector 42 (e.g. when the collector 42 is a hollow vessel). Upon reaching a particular weight, the collector 42 may be removed/exchanged from the system 10 so that the anaesthetic agent may be recovered from the collector 42.

In some embodiments, the collector 42 may have multiple stages for removing anaesthetic agents from the exhaust gas. For example, each collector 42 may include a first stage 54 and a second stage 56. The stages 54, 56 may use one or more different methods or devices for collecting or reclaiming anaesthetic agents from the exhaust gas. For example, the first stage 54 may include a first type of adsorbent material such as a molecular sieve that tends to adsorb a first type of anaesthetic agent (e.g. Sevoflurane or Desflurane, or both) for later reuse. The second stage 56 may include a second adsorbent material such as a molecular sieve that tends to adsorb a second type of anaesthetic agent (e.g. a halogenated drug such as Isoflurane) for later reuse.

Accordingly, a multi-stage collector 42 may allow the collection system 10 to collect two or more types of anaesthetic agents for later reuse. This may be useful when implementing a centralized collection system 10 that recovers anaesthetic agents from multiple sources of exhaust gas that may contain multiple different anaesthetic agents.

In some embodiments, each of the first and second stages 54, 56 may collect more than one type of anaesthetic agent. For example, the first stage 54 may collect a plurality of anaesthetic agents such as all halogenated drugs. However, even if the first stage collects a plurality of anaesthetic agents, the first stage 54 may preferentially collect one or more anaesthetic agents in comparison to other anaesthetic agents. For example, the first stage 54 may collect all halogenated drugs, but may also collect Sevoflurane and Desflurane to a greater extent than Isoflurane.

While the illustrated embodiment shows two stages 54, 56, the collector 42 may include any number of stages. For example, there may be additional stages to reclaim other anaesthetic agents for later reuse, including but not limited to other halogenated drugs or nitrous oxide. In some embodiments, the collector 42 may include a single stage.

In some embodiments, the multiple stages of the collector 42 may serve purposes other than reclaiming multiple types of anaesthetic agents for later reuse. For example, the second stage 56 may include a second adsorbent material, such as activated charcoal, that functions as a fail-safe that may help prevent at least some anaesthetic agents from exiting the collection system 10, and which could otherwise lead to pollution.

For example, activated charcoal may adsorb one or more anaesthetic agents, but it may be impractical to recover those adsorbed anaesthetic agents from the activated charcoal. In this sense, the activated charcoal may be disposable and may merely sequester the anaesthetic agents, as opposed to allowing them to be reclaimed for later reuse. Nonetheless, providing a second stage 56 with activated charcoal or similar materials may help reduce pollution and generally provide for cleaner exhaust gases.

In some embodiments, one or more collectors 42 or stages thereof may act as a sequestration device that collects anaesthetic agents for disposal, as opposed to later reuse. For example, the collector 42 may be a vessel containing activated charcoal and it may be impractical to recover the anaesthetic agents from the activated charcoal for reuse.

In some embodiments, the collection system 10 may not include a dryer 40. For example, this may be possible when the system 10 includes a collector 42 that functions relatively independent of moisture content in the exhaust gas flow, such as a molecular sieve (which could be hydrophobic). However, providing a dryer 40 may improve the efficiency of a hydrophobic molecular sieve, for example, because it has been determined that hydrophobic molecule sieves might tend to adsorb some water in addition to anaesthetic agents.

When the system 10 includes a dryer 40, it may become saturated or otherwise unable to remove moisture from the exhaust gas. Accordingly, the collection system 10 may include a dryer regeneration module 60 for removing or purging collected moisture from the dryer 40. For example, when the dryer 40 includes alumina desiccant, the regeneration module 60 may be operable to blow air through the desiccant in the dryer 40 under proper conditions that purge moisture from the dryer 40 and recharge the desiccant.

For example, the regeneration module 60 may include an inlet filter 62, a blower 64, a check valve 66 and a heater 68. In use, the blower 64 draws a purging gas such as air through the inlet filter to remove impurities that may otherwise damage the desiccant in the dryer 40. The filtered air exits the blower 64 and passes through a one-way check-valve 66 and then into the heater 68 where the air is heated to a temperature sufficient to remove moisture from the desiccant in the dryer 40. The air then proceeds through the dryer 40 and may then vent to atmosphere through the exhaust 46.

As described above, the heater 68 heats the air to a temperature sufficient to purge moisture from the desiccant. For example, the temperature may range from approximately 60° C. to 300° C. In some embodiments, the regeneration module 60 may provide air at approximately 200° C. and 20 cubic feet per minute for approximately six hours, which may be sufficient to remove moisture from approximately 7.5 kilograms of activated alumina desiccant.

In some cases, the dryer 40 is generally allowed to cool after the desiccant is purged with hot air. The cooling time may be approximately two hours. After this time, the dryer 40 may be used once again to remove moisture.

As described above, the dryer 40 may be configured to operate continuously for between about 8-16 hours after being regenerated by the dryer regeneration module 60, which may be sufficient to operate the collection system 10 for an entire day. At the end of the day, the dryer 40 may be purged of collected moisture using the process described above. This process may take approximately 8 hours, which means in some cases the system 10 can be purged at night while the system 10 is not in use. Once purged, the system 10 can resume normal operations the following day.

In some embodiments, the dryer 40 may be configured to operate for longer periods of time. In some embodiments, there may be two or more dryers 40 fluidly coupled in parallel so that the system 10 can operate continuously. In this sense, the dryers 40 may have a similar configuration to the collectors 42 described above.

When purging moisture from the dryer 40 using the regeneration module 60, the air may proceed through the dryer 40 in reverse (e.g. from the outlet of the dryer to the inlet of the dryer). For example, the regeneration module 60 may be connected to an outlet port located near the top of the dryer 40, and an inlet port on the bottom of the dryer 40 may be connected to the exhaust 46. This configuration may help purge moisture from the dryer 40 because with high down flow purge air the desiccant material may be compacted and may increase the surface area contact, which may tend to avoid channelling, fluidization and dust release from the desiccant bed.

In some other embodiments, the regeneration module 60 may blow air into the dryer 40 in the normal flow direction.

While the illustrated embodiment shows the dryer 40 having two inlet ports and two outlet ports, there may be one inlet port and one outlet port that are connected to respective components, for example, using T-connectors or manifolds.

In some embodiments, the system 10 may include control valves 50, 70, and 72 that control the direction of airflow through the dryer 40 and other elements of the system 10. These valves 50, 70 and 72 may inhibit air from flowing into the AGSS 30 or into the collectors 42 when the regeneration module 60 blows air through the dryer 40. For example, when regenerating the dryer 40, valves 50 and 72 may be closed, and valve 70 may be open. The outlet of the valve 70 may be connected to the outlet port 44 of the system 10 for venting air to atmosphere. Once the dryer 40 has been purged and regenerated, the valve 70 may be closed and the other valves 50 and 72 may be opened to resume normal operations and continue collecting or reclaiming anaesthetic agents.

In some embodiments the valves 50, 70, 72 may be manually controlled.

In some embodiments, the valves 50, 70, 72 may operate automatically. For example, the valve 72 may be a check valve. In another example, the valves may be controlled by a controller 80 or monitoring system 90 as will be described below.

In some embodiments, the controller 80 (such as a control panel) may be configured to automate the system 10. For example, the controller 80 may monitor the status of the dryer 40 and/or the status of the collectors 42 (e.g. via the sensor 52) to determine if they are full and need to be replaced or regenerated. The controller 80 may also operate the dryer regeneration module 60 and the valves 50, 70 and 72 depending on the capacity of the dryer 40. For example, there may be a sensor (e.g. similar to or the same as sensor 52) for measuring the amount of moisture collected by the dryer 40 and the controller 80 may be in communication with that sensor, for example, to operate the dryer regeneration module 60 when the dryer 40 is full or almost full.

In some embodiments, the system 10 may be manually operated. For example, the dryer regeneration module 60 and the valves 50, 70, 72 may be manually operated. The system 10 may also have both automated and manual operation modes, for example, to provide system redundancy and safety.

In some embodiments, the system 10 may include a bypass or failsafe so that exhaust gases may bypass the dryer 40 and/or collectors 42 and/or other components of the system 10. It may be desirable to use a bypass when conducting maintenance or servicing of the system 10.

For example, the collection system 10 may include a bypass valve 84 connected between the inlet port 32 and the outlet port 44. In some embodiments, the bypass valve 84 may be operated automatically. In this sense, the bypass valve 84 may be a fail-safe valve that enhances safety, such as a normally open, energized closed, spring return ball valve, piston valve, blow-off valve or a burst disc. In other embodiments, the bypass valve 84 may be operated manually.

The system may also include control valves 86, 88 that isolate the components of the system 10, for example, when the bypass valve 84 is in use. For example, valves 86, 88 may be closed when the bypass valve 84 is open. The opening and closing of the valves 84, 86, 88 may be automated and may occur at the same time or at different times.

As described above, the collection system 10 may be located centrally and remotely from one or more sources of exhaust gas (e.g. the operating rooms 12, 14 and 16). Having a centrally located system may decrease the overall cost of the collecting or reclaiming anaesthetic agents in comparison to conventional systems that are located at or near the source of the exhaust gas. As such, the initial capital costs of providing a large central collection system may be less than the accumulative cost of several smaller localized systems.

Furthermore, operational costs of a centralized system may be lower in comparison to a local system because the centralized system 10 may be able to more easily implement a monitoring system that controls the collection and reclamation of anaesthetic agents from each source of exhaust gas. Tracking the collection of multiple sources of exhaust gas may help determine when servicing or maintenance is necessary, which may result in increased uptimes. For example, the monitoring system may track the capacity of the dryer 40 and/or collectors 42 so that they may be replaced or regenerated once they are saturated or otherwise full. Monitoring one central system in this way may be less expensive than monitoring several individual localized systems.

Figure 2:
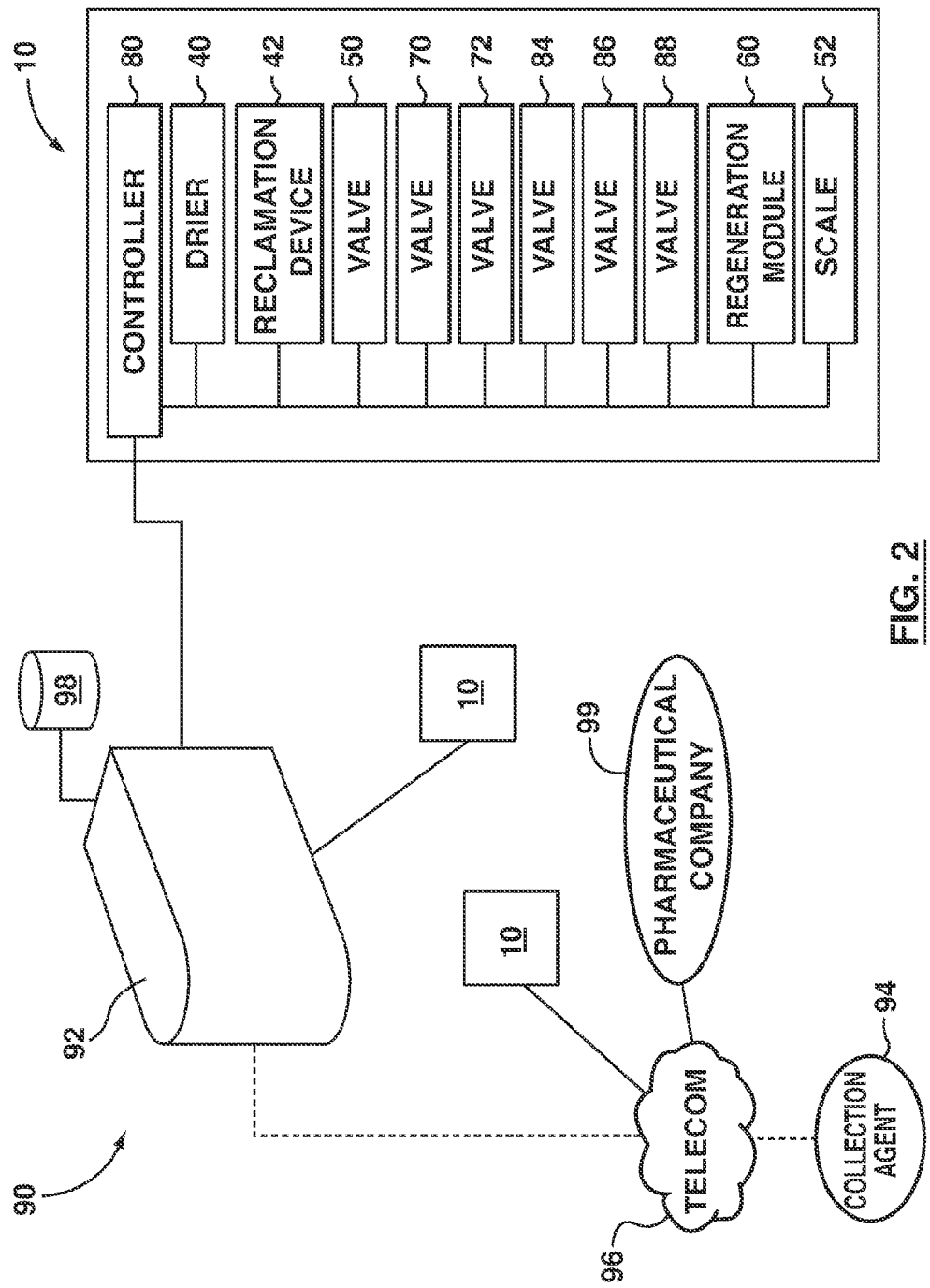
FIG. 2 is a schematic representation of a monitoring system for use with the collection system of FIG. 1.

Referring now to FIG. 2, a sample monitoring system 90 will now be described in greater detail. The monitoring system 90 generally includes a processor 92 that is in electronic communication (e.g. via a wired or wireless network) with the collection system 10 and the various subcomponents thereof such as the dryer 40, the collectors 42, the valves 50, 70, 72, the sensors 52, and the regeneration module 60.

The processor 92 may be a computer, microprocessor or another other suitable device for monitoring the collection system 10. In some embodiments, the processor 92 may be implemented in electronics that are part of the controller 80 within the system 10. In some embodiments, the processor 92 may be located separately and remotely from the collection system 10 altogether, and may be in communication with a plurality of collection systems 10 as will be described in greater detail below. In these cases, the processor 92 may be in communication with the controller 80 of each of the plurality of collection systems 10.

Generally, the processor 92 may communicate with the sensors 52 to determine when the collectors 42 are full. When the collectors 42 are full (or when the sensor 52 measures a particular amount of anaesthetic agent collected), the monitoring system 90 may initiate reclamation of the anaesthetic agent, for example, by initiating a process to purge or exchange the collector 42 that is full. For example, when using some collectors 42 with hydrophobic molecular sieves, it may be necessary to remove and/or exchange the collector 42 (e.g. a hollow vessel of hydrophobic material) from the system 10 to recover the anaesthetic agents captured therein. When one collector 42 is being removed/exchanged, the processor 92 may divert the flow of exhaust gases to one or more other collectors 42 that are still operational, for example, by opening or closing the valves 50.

Furthermore, when one or more hollow vessels are full, the monitoring system 90 may alert a collection agent 94 in order to request pick up and exchange the full vessels with empty ones. For example, the processor 92 may communicate with a third party collection agent 94 via a communications network 96 such as the Internet. After receiving the alert, the third party collection agent 94 may recover anaesthetic agents from the full vessels and may sell the anaesthetic agents back to pharmaceutical companies 99, directly to the medical facility, and so on. In some embodiments, the collection agent 94 may be an affiliate of the entity that provides the monitoring system 10 or monitoring services.

The monitoring system 90 may also be adapted to keep track of the overall amount of anaesthetic agents recovered for tax saving or other accounting purposes. For example, the amount of anaesthetic agents recovered by a particular legal entity may allow that entity to claim tax credits such as carbon credits. Being able to track these tax credits may be particularly beneficial to drug companies and hospitals and may provide financial benefits.

To keep track of this tax saving or other accounting information, the monitoring system 90 may include a data storage medium 98 such as a hard drive or database connected to the processor 92. The processor 92 may keep track of the overall amount of anaesthetic agents recovered and the storage medium 98 may store the tax savings information for later use.

The monitoring system 90 may also track the status of multiple collection systems 10. For example, there may be a plurality of medical facilities in a particular geographic area or region, with each medical facility having a centralized collection system 10. The processor 92 may be in communication with each of these collection systems 10 directly or through the communications network 96 so as to track overall collection and reclamation of anaesthetic agents for that geographic region. This information may be stored on the storage medium 98 for later use (e.g. for calculating tax credits).

In some embodiments, the monitoring system 90 may be adapted to provide supply chain management for a particular geographic region, for example, by keeping track of the demand of each healthcare facility and the amount of anaesthetic agents each healthcare facility recovers. The monitoring system 90 may then allocate the recovered anaesthetic agents to the facilities based on demand, and may order fresh anaesthetic agents (e.g. from a pharmaceutical supply company) based on demand. Accordingly, in such embodiments the processor 90 may be in communication with the pharmaceutical company 99, for example, through the communications network 96.

Figure 2A:
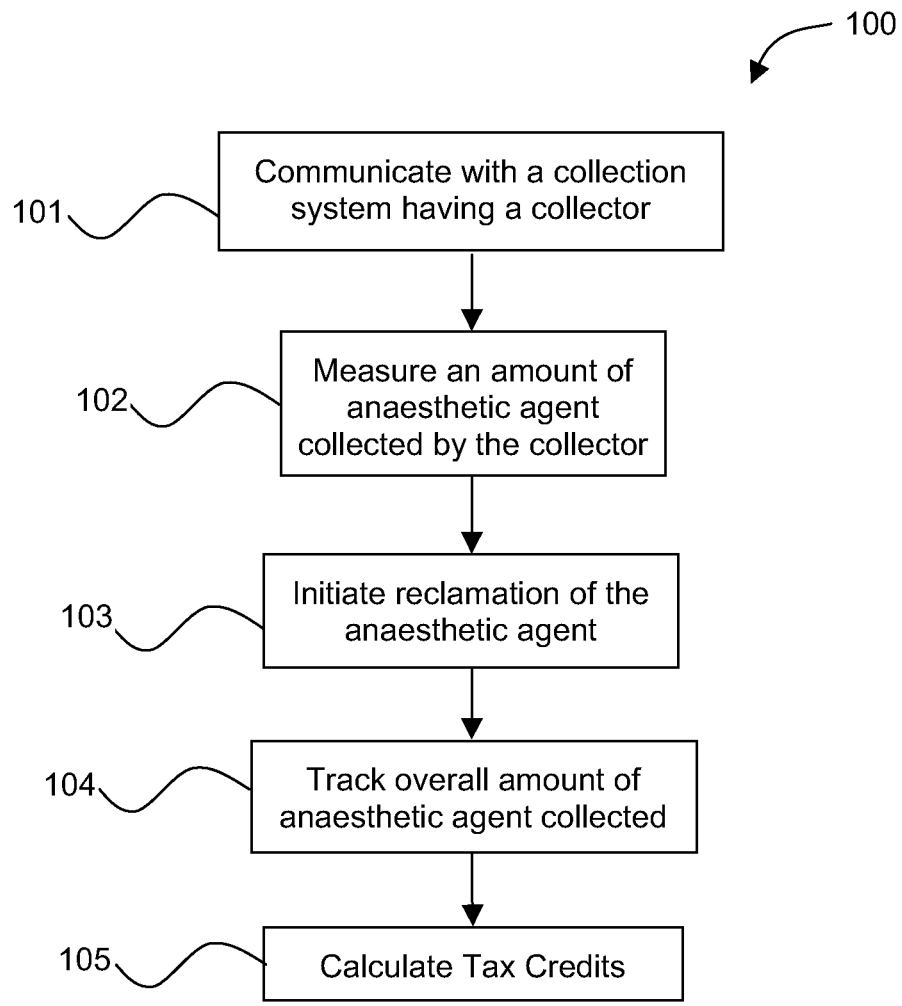
FIG. 2A is a flow chart illustrating a method for collection of anaesthetic agents according to another embodiment.

Referring now to FIG. 2A, illustrated therein is a method 100 for monitoring collection of anaesthetic agents.

Step 101 includes communicating with at least one collection system. For example, the processor 92 may communicate with the one or more collections systems over a wired or wireless communication network. The collection system(s) may be similar to the collection system 10 described above. Each collection system generally includes at least one collector (e.g. the collector 42) for collecting an anaesthetic agent from an exhaust gas that includes the anaesthetic agent. In some embodiments, step 101 may include communicating with a plurality of collection systems, which may be located remotely.

Step 102 includes measuring an amount of anaesthetic agent collected by each collector. For example, the sensors 52 may be used to measure the amount of anaesthetic agent collected by the collectors 42.

Step 103 includes initiating reclamation of the anaesthetic agent from a collector after measuring a particular amount of anaesthetic agent collected by the respective collector. For example, reclamation may be initiated when the sensor 52 detects that the respective collector 42 is full, or almost full.

Step 104 includes tracking an overall amount of anaesthetic agent collected. For example, the storage medium 98 may be used to track the overall amount of anaesthetic agent collected. Furthermore, the storage medium 98 may track the overall amount of anaesthetic agent collected by a plurality of collection systems.

Step 105 includes calculating tax credits corresponding to the overall amount of anaesthetic agent collected. For example, the processor 92 may calculate the tax credits.

Referring again to FIG. 1, as shown the collection system 10 is located downstream from the AGSS 30. Furthermore, in the illustrated embodiment, the AGSS 30 is an active system, which tends to provide a positive pressure downstream of the AGSS 30 (e.g. approximately 3 psi) and provides suction of the exhaust gas under negative pressure upstream of the AGSS 30 (e.g. approximately 12-20 inches-Hg). Connecting the collection system 10 to the exhaust side of the AGSS 30 provides an opportunity to collect anaesthetic agents under positive pressure, which may increase the efficiency of the collectors 42 because the adsorption of anaesthetic agents may be reduced under high negative pressures (e.g. 12-20 inches-Hg).

In some embodiments, the AGSS 30 may include a vacuum pump and the collection system 10 may be connected to the outlet of the vacuum pump. Accordingly, the collection system 10 might receive exhaust gases having a positive pressure, and may thereby collect aesthetic agents under positive pressure, which may increase the efficiency of the collection system 10, particularly when utilizing adsorption collectors 42 that include molecular sieves.

In some other embodiments, the collection system 10 may be located upstream of the AGSS 30. For example, the collection system 10 may be located upstream of a passive AGSS, which may provide a low negative pressure, such as approximately 0.1 inches-WC (water column).

Figure 3:
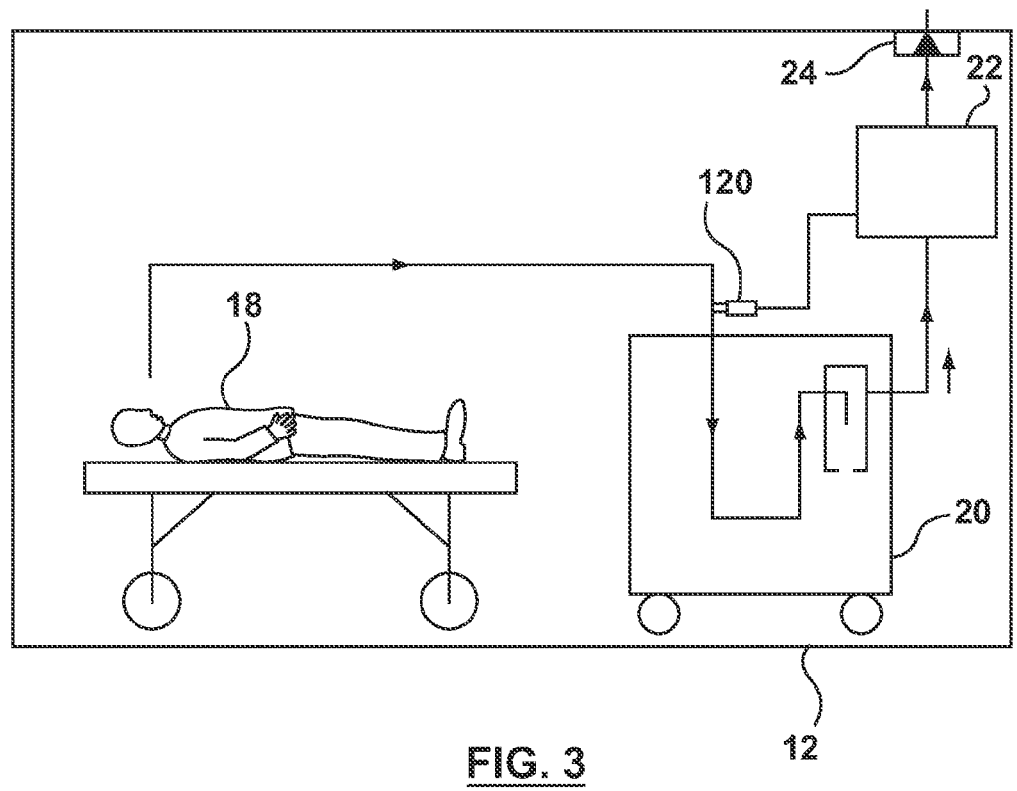
FIG. 3 is a schematic representation of an operating room and a conservation valve of the collection system of FIG. 1.
Figure 4:
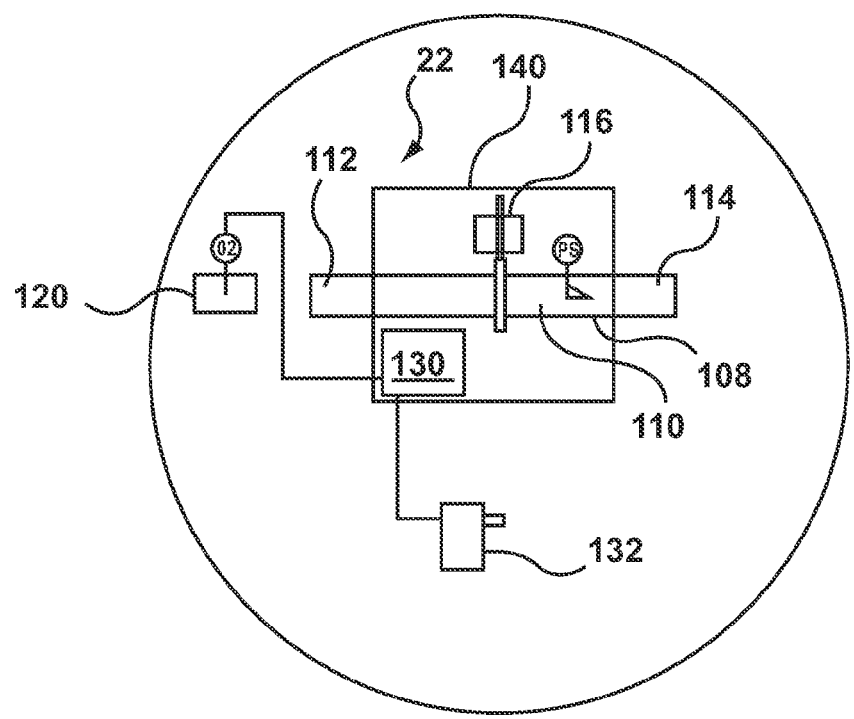
FIG. 4 is a schematic representation of the conservation valve of FIG. 3.

Referring now to FIGS. 1, 3 and 4, the conservation valve 22 will now be described in greater detail.

As shown in FIGS. 1 and 3, the conservation valve 22 is located between the AGSS 30 and the anaesthetic machine 20. The conservation valve 22 is operable to selectively open and close the fluid passage between the anaesthetic machine 20 and the AGSS 30, for example, depending on whether or not the anaesthetic machine 20 is actually in use. This may increase the efficiency of the collection system 10 and/or AGSS 30 as will be described below.

Referring now to FIG. 4, as shown the conservation valve 22 includes a valve body 108 having an inlet port 112, an outlet port 114, and a fluid passageway 110 therebetween. The conservation valve 22 also includes an actuator 116 for selectively opening and closing the fluid passageway 110 between the inlet 112 and outlet 114.

Generally, the inlet port 112 is connected to a source of exhaust gas (e.g. via the anaesthetic machine 20) so as to allow the exhaust gas to flow through the fluid passageway 110, and the outlet port 114 is connected to the collection system 10 (e.g. via the AGSS 30). The inlet 112 and outlet 114 may have connectors for connecting the conservation valve 22 to piping, tubes, or other mediums for transporting liquids or gases. For example, the inlet 112 may have a ¼-inch NPT female thread. Similarly, the outlet 114 may have a ¼-inch NPT female thread.

The actuator 116 is generally located within the fluid passageway 110 and may be any device for controlling fluid flow, such as an electronically controlled solenoid valve. In some embodiments, the actuator 116 may be a solenoid valve, a part-turn actuator such as a ball valve, or a linear actuator such as a diaphragm valve. In some embodiments, the actuator 116 may be operated by electronics, pneumatics or hydraulics.

The actuator 116 may open and close the fluid passageway 110 based on the presence or absence of exhaust gases coming from the source (e.g. the anaesthetic machine 20 or the patient 18). As such, the conservation valve 22 may include a sensor 120 that detects the presence or absence of exhaust gases so as to open and close the fluid passageway. The sensor 120 may be connected to the source of exhaust gases upstream of the valve body 108. For example, in FIG. 1, the sensor 120 is connected between the patient 18 and the anaesthetic machine 20.

In some embodiments, the sensor 120 may detect the presence or absence of one or more compounds in the exhaust gases that indicate whether or not there is a flow. For example, the sensor 120 may detect a compound such as oxygen. In particular, the percentage of oxygen in the exhaust flow may indicate whether or not a patient is breathing through the anaesthetic machine 20, and as such, may indicate whether or not the anaesthetic agent is present in the exhaust gas.

In use, the sensor 120 may measure an ambient oxygen content corresponding to an ambient condition, for example, when the anaesthetic machine 20 is not in use. The ambient oxygen content may be approximately 21%, which is typically the natural oxygen content in air. When the sensor 120 detects a change in oxygen content, for example, a measured oxygen content above the ambient oxygen (e.g. because the anaesthetic machine is supplying enriched oxygen) or below the ambient oxygen (e.g. the patient is consuming oxygen), this may indicate the anaesthetic machine is in use, and the valve 22 may be opened.

In some embodiments, the sensor 120 may continue monitoring the oxygen content to determine if ambient conditions have re-established such that measured oxygen content returns to approximately the ambient oxygen content, which may indicate the anaesthetic machine 20 is no longer in use. If this occurs, the valve 22 may be closed.

In some embodiments, the valve 22 may open and close based on a measured oxygen content falling within a range around the ambient oxygen content. For example, the range may account for error tolerances in the sensor 120, such as an error of plus or minus approximately 10%. In some embodiments, the range may be approximately 19% to 23% oxygen content when the ambient oxygen content is 21% and the valve 22 may open when the oxygen content falls outside of the 19% to 23% range. The range may also be selected to account for the amount of oxygen a patient consumes, which may be approximately 5%.

In some embodiments, the sensor 120 may measure the oxygen content after a period of time or over a particular time interval. For example, after opening the valve based on a change in the measured oxygen content, the sensor 120 may measure the oxygen content every sixty seconds, or may measure and calculate the average oxygen content over sixty seconds. This may help account for fluctuations in the oxygen content, which may be associated with error tolerances for the sensor 120, changes in the patient's breathing, or other factors. In some embodiments, the time period or time interval may be longer or shorter than sixty seconds. For example, in some instances the time period or time interval may be between approximately ten seconds and five minutes.

After the valve 22 opens, the valve 22 may remain open for a particular waiting period even if the measured oxygen content returns to a level corresponding to the ambient oxygen content or an appropriate range. For example, in some instances the waiting period may be any time between approximately one minute and approximately one hour. In some particular embodiments, the waiting period may be approximately one minute.

Providing a waiting period may help reduce the possibility of closing the valve prematurely, for example, when the sensor 120 makes an erroneous measurement.

In some embodiments, the sensor 120 may detect other compounds, such as anaesthetic agents or carbon dioxide. In some embodiments, the sensor 120 may detect a flow or change in pressure as a trigger for opening and closing the valve.

Referring to FIG. 4, the conservation valve 22 may also include a processor 130 for controlling the actuator 116 based on conditions detected by the sensor 120. The conservation valve 22 may also include a power supply 132 for providing power to the processor 130, the sensor 120 and the actuator 116.

As shown, in some embodiments, one or more subcomponents of the conservation valve 22 may be located inside a housing 140, which may be made of metal, plastic, or another suitable material. For example, the valve body 108, the actuator 116, and the processor 130 may be located inside the housing 140, while the sensor 120 and the power supply 132 may be located outside the housing 140. In some embodiments, the sensor 120 and the power supply 132 may also be located inside the housing 140.

The conservation valve 22 may tend to increase efficiency of the AGSS 30. For example, if the AGSS 30 operates continuously, it may operate even when the anaesthetic machine 20 is turned off and there are no anaesthetic agents in the flow. This may waste power and reduce efficiency, as the AGSS 30 will be processing gas even when no anaesthetic agents are present.

In contrast, the conservation valve 22 may isolate the source of exhaust gas from the AGSS 30 when the anaesthetic machine 20 is turned off. This may increase the efficiency of the AGSS 30 because the power source may not have to work as hard when one or more conservation valves 22 are closed.

In some embodiments, the conservation valves may also allow the AGSS 30 to shut off when one or more (e.g. all) of the anaesthetic machines 20 are turned off. This may further increase the efficiency of the AGSS 30.

The conservation valve 22 may also increase the efficiency of the collection system 10 by isolating the sources of exhaust gas from the collection system 10 when the anaesthetic machine 20 is turned off and there are no anaesthetic agents in the exhaust gas flow.

More particularly, the conservation valve 22 may increase the efficiency of the dryer. For example, when there are no anaesthetic agents in the exhaust gas flow, the dryer 40 may unnecessarily remove moisture. Closing the conservation valve 22 tends to isolate these inactive sources from the dryer 40, which may increase the potential operation time for the dryer 40 and may reduce the need to purge and regenerate the dryer 40.

The conservation valve 22 may also increase the efficiency of the collectors 42. For example, when room air (without anaesthetic agents) flows through collectors 42 that use adsorbent material, the clean air may displace captured anaesthetic agents and carry those anaesthetic agents to the exhaust 46. This may have the undesired effect of purging the collector 42 of anaesthetic agents, which may reduce the collection efficiency of the collectors 42. Closing the conservation valves 22 tends to reduce the amount of room air that is processed by the collectors 42 and may prevent unintentional purging.

Figure 5:
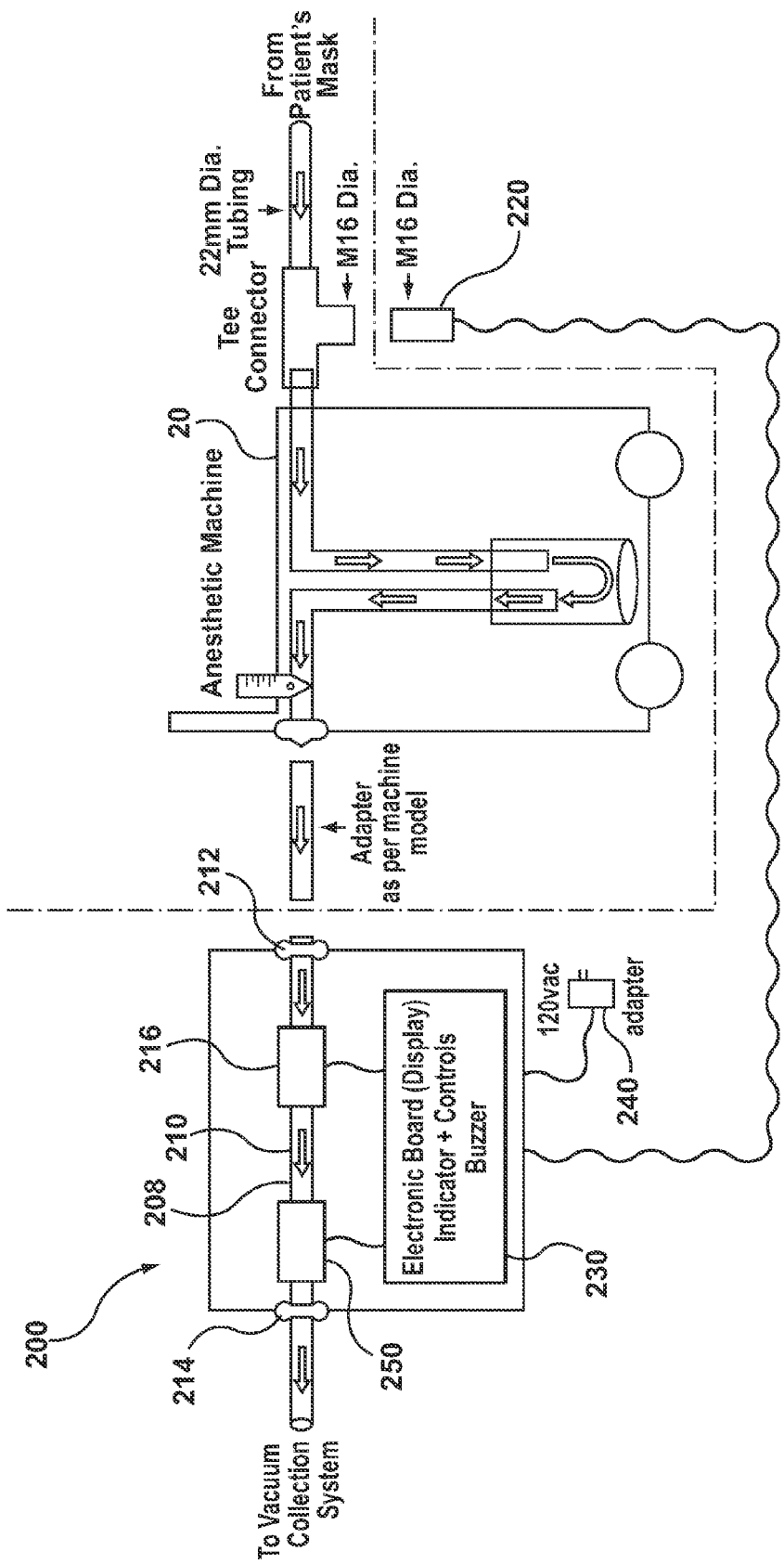
FIG. 5 is a schematic representation of a conservation valve connected to an anaesthetic machine according to another embodiment.

Referring now to FIG. 5, illustrated therein is a conservation valve 200 connected to an anaesthetic machine 20 according to another embodiment. The conservation valve 200 is similar in many respects to the conservation valve 22, and where suitable, similar elements are given similar reference numerals incremented by one hundred.

One difference is that the conservation valve 200 includes a flow sensor 220 for measuring the flow of exhaust gas from the anaesthetic machine 20. The flow sensor 220 may control the operation of the actuator 216 to selectively open and close the fluid passageway 210 based on the presence or absence of fluid flow.

As shown, the flow sensor 220 is located upstream of the valve body 208. For example, the flow sensor 220 may be connected to the inlet of the anaesthetic machine 20 and may receive exhaust gases from a patient. The flow sensor 220 may measure the flow rate in terms of volume or mass of the exhaust gas. If the flow rate drops below a certain threshold, the flow sensor 220 may trigger the actuator 216 to close. If the flow rate exceeds a certain threshold, the flow sensor 220 may trigger the actuator 216 to open.

The flow sensor 220 may also include a pressure sensor, which may help indicate whether or not the anaesthetic machine 20 is in use when the actuator 216 is in the closed position. If the pressure exceeds a certain threshold, the flow sensor 220 may trigger the actuator 216 to open.

In some embodiments, the flow sensor 220 may communicate with the actuator 216 via the processor 230. In other embodiments, the flow sensor 220 may communicate directly with the actuator 216.

In some embodiments, the flow sensor 220 may cooperate with another sensor to determine the presence or absence of exhaust gas flowing from the source. For example, the processor 230 may determine if there is a flow of exhaust gas based on both the flow rate from the flow sensor 220 and the content of a particular compound in the flow as determined by the other sensor (e.g. the sensor 120). This may be useful when there is ambient flow through the anaesthetic machine 20 but anaesthetic agents are not being delivered to the patient.

The conservation valve 220 may also include a switch 250 (e.g. a flow switch or limit switch) connected to the valve body 208 within the fluid passageway 210 between the inlet 212 and the outlet 214, and downstream of the actuator 216. A flow switch helps determine whether the actuator 216 is open or closed based on the presence or absence of a flow after the actuator 216, and as such, the flow switch tends to confirm whether the valve 200 is operational. In contrast, a limit switch helps determine whether the actuator 216 is open or closed based on the position of the actuator 216, and as such, the limit switch tends to confirm whether the valve 200 is operational in a different way compared to the flow switch.

Turning now generally to FIGS. 6 to 10, in some embodiments it may be desirable that at least some nitrous oxide gas be removed from the exhaust gases before venting the exhaust gases to atmosphere. Nitrous oxide is a greenhouse gas believed to account for a significant proportion of atmospheric heating effects, as well as cause ozone depletion. Furthermore, producing nitrous oxide can be expensive. Accordingly, it may be beneficial if at least some nitrous oxide can be removed and/or collected (e.g. for reuse) as opposed to being vented to atmosphere.

Figure 6:
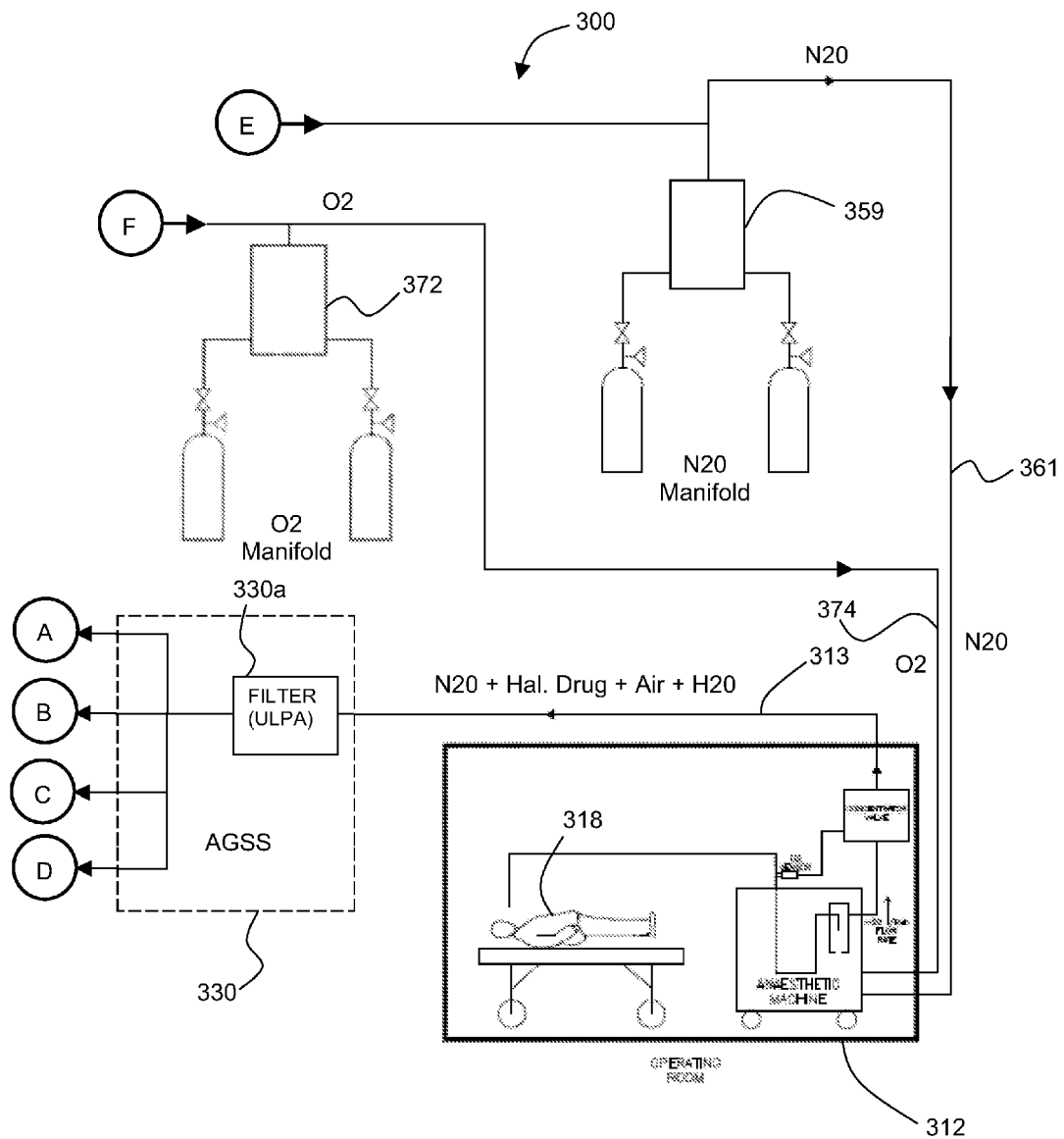
FIG. 6 is a schematic representation of a first subsystem of a collection system for collecting anaesthetic agents.

Turning now specifically to FIG. 6, illustrated therein is a first subsystem 300 of a system for collecting anaesthetic agents, and which is configured to cooperate with one or more other subsystems (as described in FIGS. 7 to 10) for removing at least some of the nitrous oxide prior to venting to atmosphere.

As shown, the first subsystem 300 includes an AGSS 330 (which may be the same as or similar to the AGSS 30 as generally described above). The AGSS 330 is in fluid communication (e.g. via piping 313) with one or more sources of exhaust gases, such as one or more operating rooms 312 having one or more patients 318 therein. As shown the piping 313 allows exhaust gases to pass from the operating rooms 312 to the AGSS 330, including nitrous oxide ($N_2O$), anaesthetic agents such as halogenated drugs (Hal. Drugs or HD), water or moisture ($H_2O$), and optionally in some cases air.

In turn, the AGSS 330 is in fluid communication with one or more other subsystems. For example, as indicated by reference numeral "A", in some embodiments the AGSS 330 may communicate with a second subsystem 302 shown in FIG. 7. Similarly, as indicated by reference numeral "B", in some embodiments the AGSS 330 may communicate with a third subsystem 304 shown in FIG. 8. Furthermore, as indicated by reference numeral "C", in some embodiments the AGSS 330 may communicate with a fourth subsystem 306 shown in FIG. 9. Finally, as indicated by reference numeral "D", in some embodiments the AGSS 330 may communicate with a fifth subsystem 308 shown in FIG. 10.

In some embodiments, the AGSS 330 may include one or more filters 330a for filtering the incoming exhaust gases. For example, the filters 330a could be ultra-low particulate air (ULPA) filters. In other embodiments, the filters 330a could be high efficiency particulate air (HEPA) filters.

In some embodiments, a Med Vac may be used as the AGSS 330.

Figure 7:
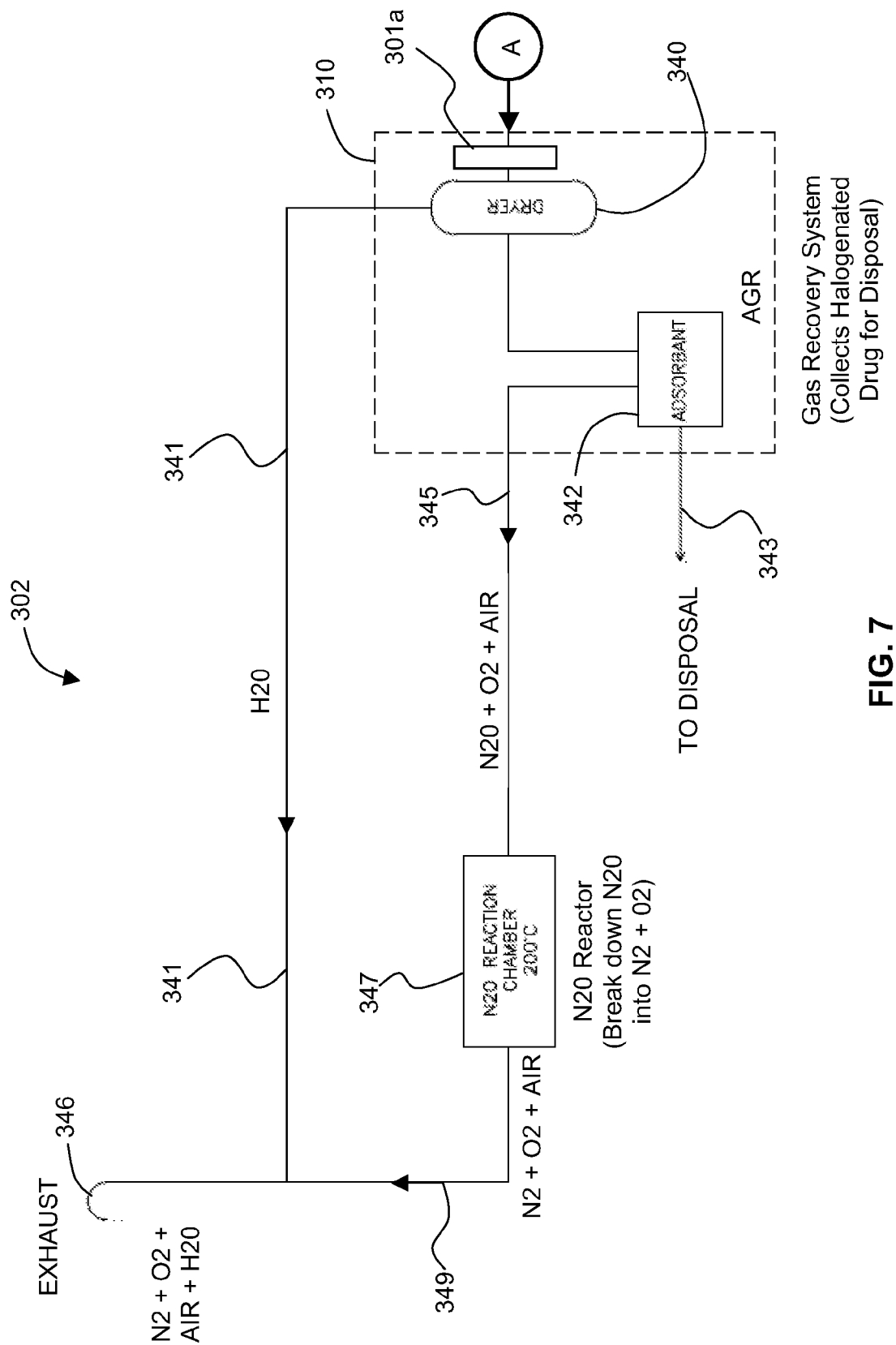
FIG. 7 is a schematic representation of another subsystem for use with the first subsystem of FIG. 6, and which is operable to remove nitrous oxide from exhaust gases using a reaction chamber.

Turning now specifically to FIG. 7, as shown therein the second subsystem 302 is operable remove at least a portion of the nitrous oxide from the exhaust gases before venting at least some of those gases to atmosphere.

The second subsystem 302 includes a collection system 310, which may be similar to or the same as the collection system 10 as generally described above, and which is operable to receive gases from the AGSS 330. For example, the collection system 310 may include components such as a dryer 340 (which could be the same as or similar to the dryer 40 as described above) for removing moisture from the incoming exhaust gases, and one or more collectors 342 located downstream from the dryer 340 for collecting and removing anaesthetic agents from the exhaust gas. In some embodiments, the collectors 342 could be the same as or similar to the collectors 42 as generally described above.

In this embodiment, the collector 342 is shown as an adsorbent collector although other collectors could also be used.

In some embodiments, the collection system 310 may include one or more filters 301a for filtering the incoming gases, such as a ULPA or HEPA filter. As shown, the filters 301a may be provided upstream of the dyer 340 and collector 342.

As shown, moisture removed by the dryer 340 can be vented to atmosphere via an exhaust 346 (coupled to the dryer 340 via a fluid conduit or piping 341). Furthermore, in this embodiment, the anaesthetic agents collected using the collectors 342 are sent for disposal (e.g. via a fluid conduit or piping 343). For example, in some embodiments the anaesthetic agents may be collected in large (e.g. 45-gallon) drums and then shipped to a disposal facility.

As shown, in this embodiment, the gas products exhausted by the collectors 342 are sent via piping 345 to one or more reaction chambers 347. Generally, each reaction chamber 347 is operable to decompose the nitrous oxide ($N_2O$) into its component parts, namely nitrogen gas ($N_2$) and oxygen ($O_2$), according to the following relationship:

$$N_2O \rightarrow N_2 + \tfrac{1}{2}O_2$$

For example, the reaction chamber 347 may operate at an elevated temperature to heat the incoming nitrous oxide and encourage the decomposition of the nitrous oxide into nitrogen gas and oxygen. In some embodiments the reaction chamber 347 may be operated at temperatures of around 200 degrees Celsius. In other embodiments, the reaction chamber 347 may be operated at higher or lower temperatures.

In some embodiments, one or more catalysts may be provided to the reaction chamber 347 to facilitate driving the decomposition of the nitrous oxide into nitrogen and oxygen. For example, the catalyst may include precious metals (e.g. platinum, palladium, rhodium, etc.) or metal oxides (e.g. cupric oxide, chromium oxide, ferric oxide, etc.).

By breaking down the nitrous oxide into its component parts, at least some of the nitrous oxide that would otherwise be vented to atmosphere through the exhaust 346 can be converted into other (less damaging) gases. As such, the gases sent via piping 349 from the reaction chamber 347 to the exhaust 346 will tend to include reduced amounts of nitrous oxide (and in some events, may be substantially or even completely stripped of nitrous oxide).

Figure 8:
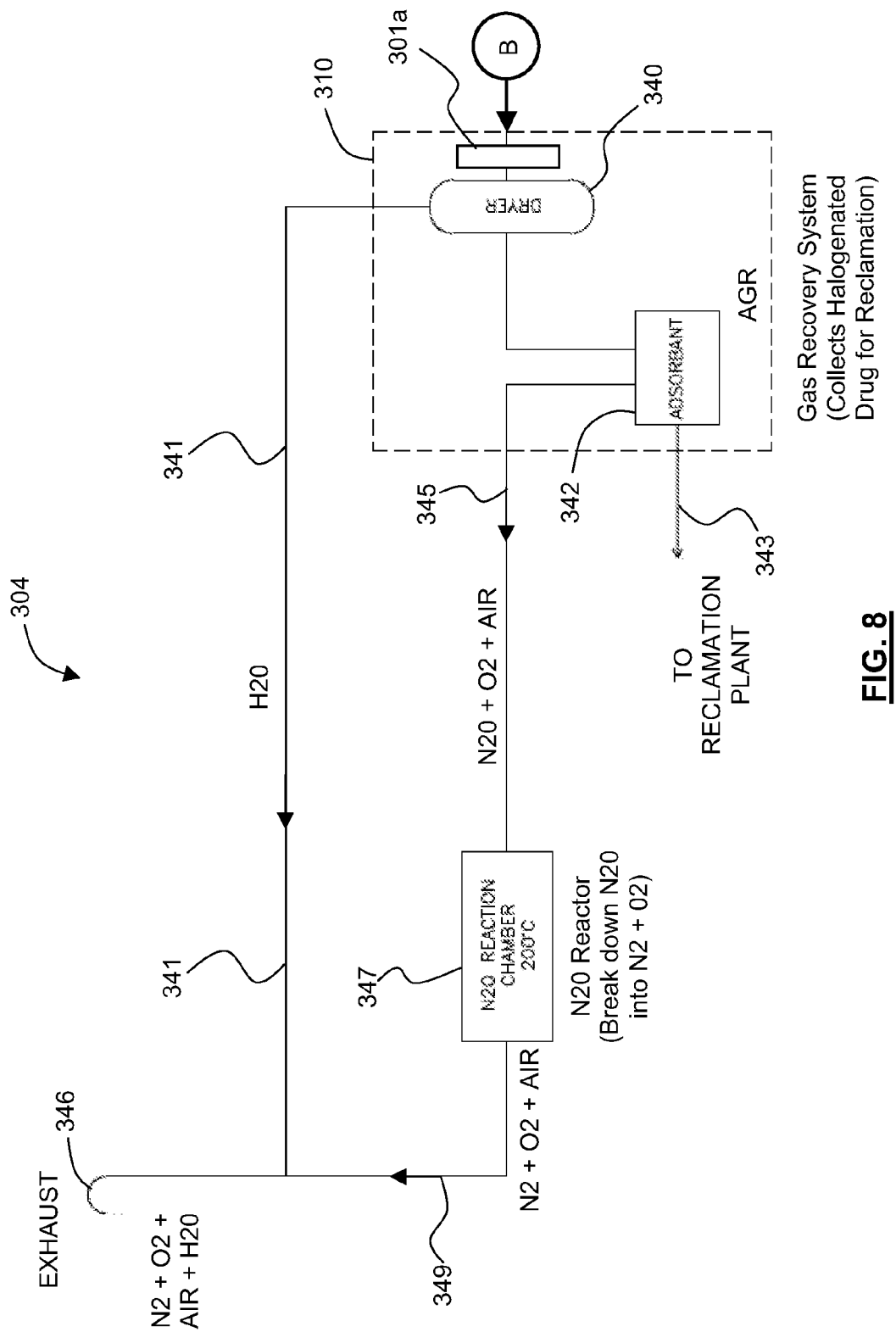
FIG. 8 is a schematic representation of another subsystem for use with the first subsystem of FIG. 6, and which is operable to remove nitrous oxide from exhaust gases using a reaction chamber.

Turning now specifically to FIG. 8, the third subsystem 304 is also operable to work with the first subsystem 300 for removing at least a portion of the nitrous oxide from the exhaust gases. Generally, the third subsystem 304 is substantially similar to the second subsystem 302 as shown in FIG. 7, except that in this embodiment, the anaesthetic agents collected using the one or more collectors 342 are sent for reclamation (e.g. via piping 343 to a reclamation plant) instead of for disposal. In some embodiments the anaesthetic agents may be collected in large (e.g. 45-gallon) drums and then shipped to a reclamation facility.

Figure 9:
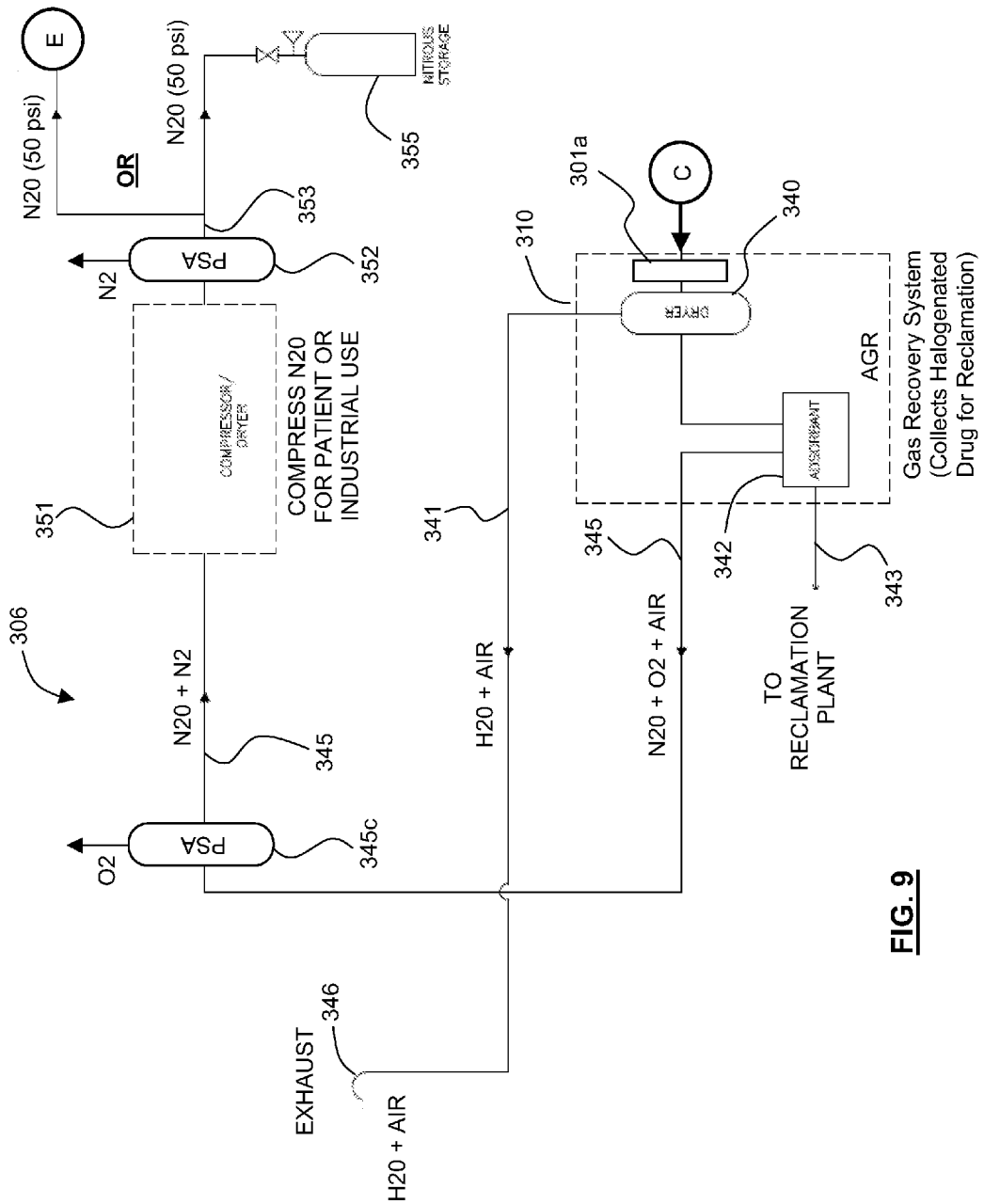
FIG. 9 is a schematic representation of another subsystem for use with the first subsystem of FIG. 6, and which is operable to remove and collect nitrous oxide.

Turning now specifically to FIG. 9, as shown therein the fourth subsystem 306 is also operable to work with the first subsystem 300 for removing at least a portion of the nitrous oxide from the exhaust gases. The fourth subsystem 306 may include elements similar to the second subsystem 302 and third subsystem 304, including a collection system 310 having a dryer 340 and one or more collectors 342.

However, in this embodiment the gases exiting the collectors via piping 345 are sent to a compressor 351 or other similar component, and are not sent to a reaction chamber 347.

The compressor 351 is operable to compress the gas mixture, which may result in higher concentrations of nitrous oxide. The compressed nitrous oxide gas is then sent via piping 353 to a nitrous storage module 355, or alternatively (as indicated by reference numeral "E") to a nitrous oxide manifold 359 shown in FIG. 6.

In some embodiments, a Pressure Swing Adsorption (PSA) or other module 352 may be provided downstream of the compressor 351 to help remove nitrogen gas from the nitrous oxide gas stream. In some embodiments, a PSA module 345c may be provided upstream of the compressor 351 to help remove oxygen gas from the gas stream prior to compression in the compressor 351.

The nitrous storage module 355 may collect nitrous oxide for subsequent processing off-site so that the nitrous oxide may eventually be reused.

The nitrous oxide manifold 359 may be located on-site at the medical facility (in some embodiments) and includes one or more storage tanks. The nitrous oxide manifold 359 may be used to supply nitrous oxide (e.g. via one or more pipes 361) to one or more patients 318 in one or more operating rooms 312 during subsequent medical procedures.

In some embodiments, one or more cleaning or purification steps may be performed at the nitrous oxide manifold 359 to ensure that the nitrous oxide gas collected therein is suitable for subsequent usage (e.g. up to medically acceptable regulatory standards). For example, the purification steps may include removal of carbon dioxide using a carbon dioxide filter (e.g. a soda lime filter).

By collecting and storing the nitrous oxide gases (e.g. either in the manifold 359 or storage module 355), as opposed to venting the nitrous oxide to atmosphere, undesired pollution tends to be reduced. Furthermore, the nitrous oxide can be reused for subsequent medical procedures, which may result in cost savings.

Figure 10:
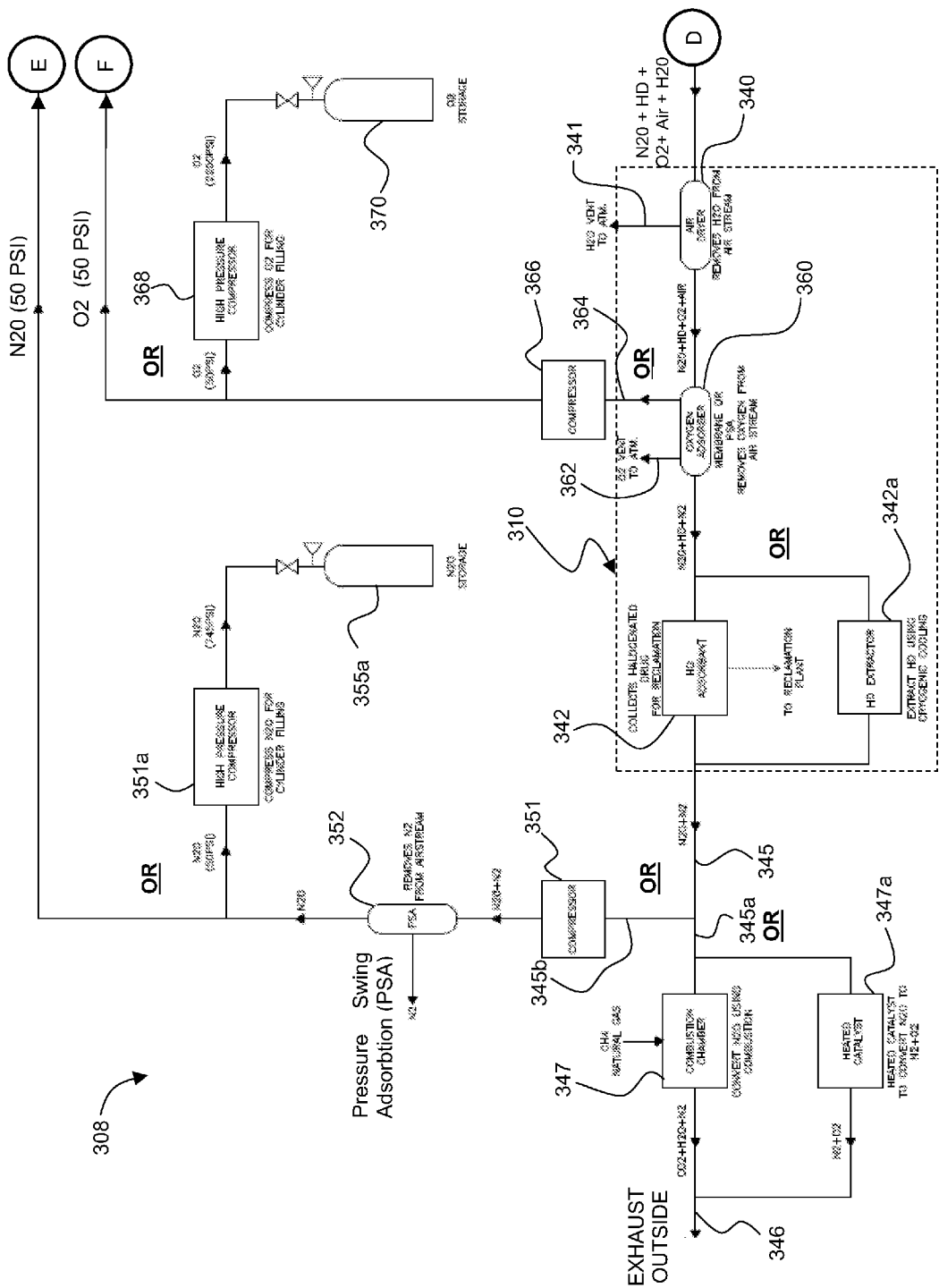
FIG. 10 a schematic representation of another subsystem for use with the first subsystem of FIG. 6, and which is operable to remove nitrous oxide and oxygen from exhaust gases.

Turning now specifically to FIG. 10, as shown therein the fifth subsystem 308 is also operable to work with the first subsystem 300 for removing at least a portion of the nitrous oxide from the exhaust gases. The fifth subsystem 308 may include many elements similar to the second subsystem 302, third subsystem 304, and fourth system 306, such as a collection system 310 having a dryer 340 and one or more collectors 342 (e.g. an adsorbent collector 342 or cryogenic collector 342a).

Similar to as described above with respect to FIG. 7, and as shown in FIG. 10, at least some of the gases exiting the collectors 342 may be fed via piping 345a to one or more reaction chambers 347 operable to decompose the nitrous oxide into nitrogen gas and oxygen. For example, as shown the reaction chamber 347 may be a combustion chamber that is heated and fed a stream of combustible gas, such as methane gas ($CH_4$) or another hydrocarbon, to encourage the decomposition of nitrous oxide. In other embodiments, the reaction chamber 347 may include a reaction chamber 347a having a heated catalyst therein for encouraging the decomposition of the nitrous oxide.

Furthermore, as described above with respect to FIG. 9, and as shown in FIG. 10, in some embodiments at least some of the gases exiting the collectors 342 may be fed via piping 345b to one or more compressors 351 so that they may be compressed for storage for subsequent use. In some embodiments, a PSA module 352 may be provided downstream of the compressor 351 to help remove nitrogen gas from the gas stream.

In some embodiments, after the PSA module 352, at least some of the gas stream may be sent to the nitrogen manifold 359 shown in FIG. 6. In other embodiments, at least some of the gas downstream from the PSA module 352 may be sent to a high pressure compressor 351a for additional compression (e.g. in some examples, to approximately 745 psi, or higher or lower pressures) for storage in a high pressure storage tank 355a. In some embodiments, the high pressure compressor 351a may be used on its own without the first compressor 351.

As shown, in this embodiment the fifth subsystem 308 also includes an oxygen collector 360 for removing oxygen from the gas stream, which may be located upstream of the reaction chamber 347. It has been discovered that removing the oxygen (e.g. using an oxygen collector 360 as shown) can further facilitate driving the decomposition of nitrous oxide into nitrogen and oxygen in the reaction chambers 347. Accordingly, extracting oxygen from the gas stream may further facilitate providing exhaust gases with at least some of the nitrous oxide removed.

As shown, the oxygen collector 360 may be positioned downstream of the air dryer 340 and upstream of the one or more collectors 342. In some embodiments, the oxygen collector 360 could include an adsorbent material for removing the oxygen. In some embodiments, the oxygen collector 360 could include a membrane separator for removing oxygen from the gas stream. In some embodiments, the oxygen collector 360 could include a Pressure Swing Adsorption (PSA) module.

As shown, in some embodiments the oxygen collected by the oxygen collector 360 may be vented to atmosphere via piping 362.

In other embodiments, the oxygen can be collected for subsequent use. For example, the oxygen may be sent via piping 364 to a compressor 366 where it may be compressed (e.g. to approximately 50 psi). The compressed oxygen may then be sent (as shown by reference character "F") to an oxygen manifold 372 shown in FIG. 6. The oxygen manifold 372 may in turn be used to supply oxygen (e.g. via one or more pipes 374) to one or more patients 318 in one or more operating rooms 312 during subsequent medical procedures.

In some embodiments, one or more cleaning or purification steps may be performed at the oxygen manifold 372 to ensure that the oxygen gas collected therein is suitable for subsequent usage. For example, the purification steps may include removal of carbon dioxide using a carbon dioxide filter (e.g. a soda lime filter).

In some embodiments, the compressed oxygen may be further compressed in a high pressure compressor 368 (e.g. in some examples to a pressure of around 2200 psi, or higher or lower pressures) and then stored in a high pressure storage tank 370 for subsequent use. In some embodiments, the high pressure compressor 368 may be used on its own without the first compressor 366.

By collecting and storing the oxygen (e.g. either in the oxygen manifold 372 or storage tank 370), the oxygen can be reused for subsequent medical procedures, which may result in cost savings.

Figure 11:
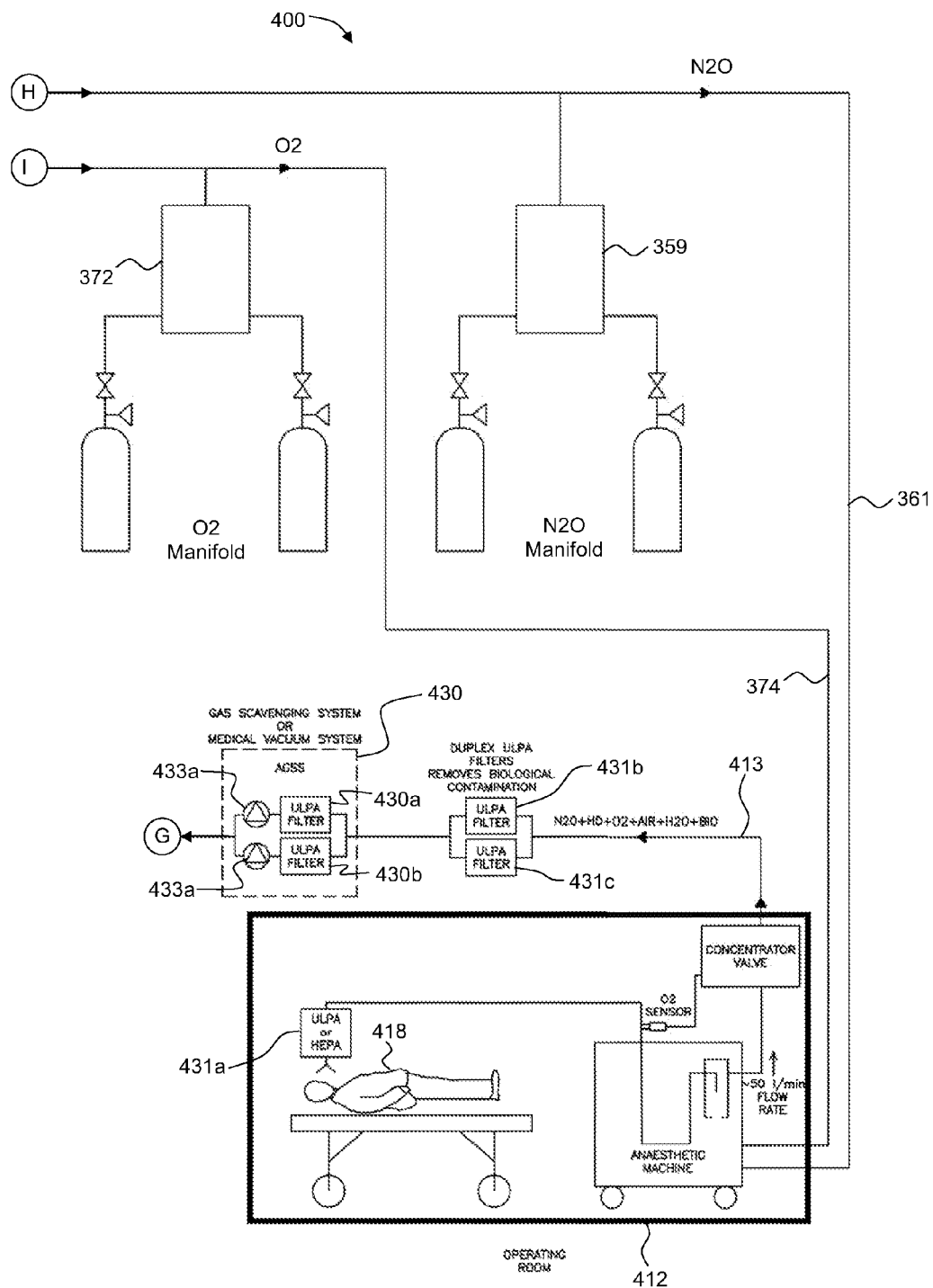
FIG. 11 is a schematic representation of a first subsystem of a yet another collection system for collecting anaesthetic agents, and which is operable to remove biological substances.
Figure 12:
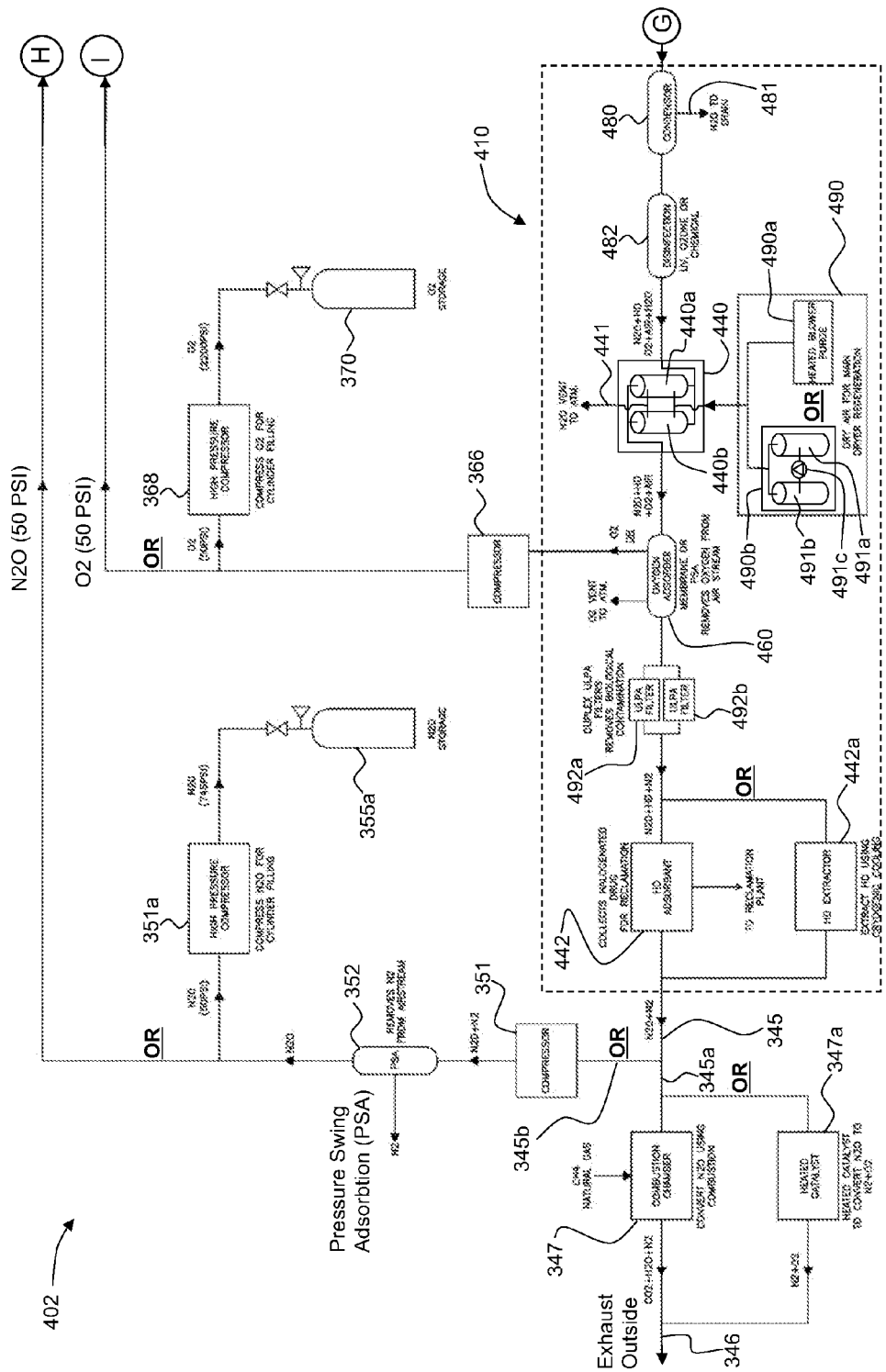
FIG. 12 a schematic representation of another subsystem for use with the first subsystem of FIG. 11, and which is operable to disinfect exhaust gases prior to collecting the anaesthetic agents.

Referring now to FIGS. 11 and 12, illustrated therein is a system for collecting anaesthetic agents, including a first subsystem 400 and a second subsystem 402.

Referring to FIG. 11, the first subsystem 400 may include elements similar to the first subsystem 300 shown in FIG. 6, such as the nitrous oxide manifold 359, the oxygen manifold 372, and piping 361 and 374. The manifolds 359 and 373 may be in fluid communication with the second subsystem 402 as generally indicated at reference numerals "H" and "I" respectively, or another subsystem (e.g. subsystem 306 or subsystem 308).

The first subsystem 400 also includes an AGSS 430 (e.g. similar to the AGSS 30 or the AGSS 330) in fluid communication via piping 413 with one or more sources of exhaust gases, such as one or more operating rooms 412 having one or more patients 418 therein. The exhaust gases may include nitrous oxide ($N_2O$), anaesthetic agents such as halogenated drugs (Hal. Drugs or HD), water or moisture ($H_2O$), biological substances (BIO), and in some cases air.

One difference is that the first subsystem 400 includes at least one filter (e.g. filters 431a, 431b, and/or 431c) between the patient 418 and the AGSS 330 for filtering incoming exhaust gases, for example, to remove particulates such as the biological substances. In particular, the patient 418 might expel biological substances, which might be entrained within the exhaust gases. If left unfiltered, these biological substances might contaminate the overall system and may interfere with system operation, including the collection of anaesthetic agents and/or extraction of nitrous oxide. Furthermore, health regulations might prohibit the subsequent sale or use of collected anaesthetic agents if there are biological substances in the collected anaesthetic agents.

As shown in FIG. 11, the subsystem 400 includes one filter 431a within the operating room 412 (e.g. proximal to a mask on the patient), and a bank of two filters 431b and 431c outside the operating room 412.

Providing filters inside the operating room 412 (e.g. filter 431a) permits early filtration of exhaust gases, which might improve system operation (e.g. collection efficiency). Furthermore, providing filters inside the operating room 412 might also enable medical staff to replace filters within the operating room 412, for example, so that a new filter may be used for each particular patient.

Providing filters outside the operating room 412 (e.g. filters 431b and 431c) might allow centralized filtration of exhaust gases, which might reduce operating costs, and might increase filtration efficiency. Furthermore, providing a bank of at least two filters fluidly coupled together in parallel (e.g. filters 431b and 431c) may provide system redundancy, and may allow one filter (e.g. filter 431a) to be operational while the other filter (e.g. filter 431b) is being replaced.

While the filters 431a, 431b and 431c are shown in FIG. 11 as having particular locations, in other embodiments, the filters may have other locations. For example, some filters (e.g. filters 430a and 430b) may be located within or after the AGSS 430. The subsystem 400 may also include more or less filters than shown.

The filters 431a, 431b, and 431c may be the same, similar, or different types of filters. For example, one or more of the filters may be ultra-low particulate air (ULPA) filters, and one or more of the filters may be high efficiency particulate air (HEPA) filters.

The filters of the first subsystem 400 are also arranged in a plurality of stages, including, a first stage filter (e.g. filter 431a) followed by a second stage filter (e.g. the bank of filters 431b and 431c) downstream of the first stage filter. Providing two or more stages of filters may improve filtration of exhaust gases. For example, the first stage (e.g. filter 431a) may include a first type of filter (e.g. a HEPA filter), which may remove certain types of substances (e.g. a first type of particulate or biological substance), and the second stage (e.g. filters 431b and 431c) may include a second type of filter (e.g. a ULPA filter), which may remove other substances (e.g. a second type of particulate or biological substance).

Another difference between the subsystem 400 and the subsystem 300 is that the AGSS 430 includes a bank of at least two filters 430a and 430b (e.g. similar to the bank of filters 431a and 431b). This allows one filter (e.g. filter 430a) to be operational while the other filter (e.g. filter 430b) is being replaced, for example.

Furthermore, each filter in the AGSS 430 may be connected to a respective power source 433a and 433b (e.g. a vacuum pump, blower or fan). Each power source may be turned on when the respective filter is installed and operational, and may be turned off when the respective filter is inoperative (e.g. being replaced).

In some embodiments, the subsystem may only include one bank of filters (e.g. the bank of filters 430a and 430b in the AGSS 430).

The outlet of the AGSS 430 is in fluid communication with one or more other subsystems. For example, as indicated by reference numeral "G", in some embodiments the AGSS 430 may communicate with a second subsystem 402 shown in FIG. 12. In some embodiments, the AGSS may be in fluid communication with other subsystems, such as the subsystems 302, 304, 306 and 308 described previously.

Referring now to FIG. 12, the second subsystem 402 generally receives exhaust gases from the first subsystem 400 as indicated by the reference numeral "G". In other embodiments, the second subsystem 402 may receive exhaust gases from other subsystems (e.g. the subsystem 300).

The second subsystem 402 may include many elements similar to the second subsystem 302, third subsystem 304, fourth subsystem 306, and fifth subsystem 308, such as a collection system 410 (e.g. similar to the collection systems 10 and 310), one or more reaction chambers 347 (e.g. a combustion chamber 347 or a catalytic reaction chamber 347a) for decomposing nitrous oxide, one or more compressors (e.g. compressors 351 or 351a for compressing nitrous oxide, or compressors 366 or 368 for compressing oxygen), one or more PSA modules 352 (e.g. for removing nitrogen gas), and one or more storage tanks (e.g. a nitrous oxide storage tank 355a or an oxygen storage tank 370). The second subsystem 402 may also supply extracted nitrogen and/or oxygen to the first subsystem 400, or another subsystem (e.g. the subsystem 300), as generally indicated at reference numerals "H" and "I".

As indicated above, the collection system 410 may include many elements similar to the collection systems 10 and 310, such as a dryer 440, one or more collectors 442 (e.g. an adsorbent collector 442 and/or cryogenic collector 442a), and an oxygen collector 460.

One difference between the subsystem 402 and the subsystem 302 is that the collection system 410 also includes a condenser 480 and a disinfection module 482 located upstream of the collectors 442.

The condenser 480 removes moisture from the exhaust gases, and outputs a dehumidified exhaust gas. The condenser 480 may expel the extracted moisture (e.g. through a drain 481). The condenser 480 may be a heat-exchanger having a coolant flowing therethrough for cooling the exhaust gases so as to condense and extract the moisture. In some embodiments, the condenser 480 may be configured to extract a substantial portion of the moisture, for example, so that the dryer 440 has substantially less moisture to extract. Extracting the moisture from the exhaust gases may also improve efficiency of the disinfection module 482 as will be described below.

The disinfection module 482 disinfects (e.g. sterilizes) the exhaust gases by eliminating one or more life forms such as microorganisms (e.g. bacteria, viruses, and fungi) and outputs a disinfected exhaust gas (e.g. to the dryer 440). More particularly, the disinfection module 482 may eliminate life forms that remain in the exhaust gas after the exhaust gas has been filtered by the upstream filters (e.g. filters 430a, 430b, 431a, 431b, or 431c of the first subsystem 400). For example, the upstream filters may remove larger biological substances (e.g. larger spores, paramecium, bacteria, viruses, etc), but might not remove smaller biological substances (e.g. small bacteria and viruses). Accordingly, the disinfection module 482 may be configured to eliminate these smaller biological substances.

In some embodiments, the disinfection module 482 may utilize a non-contact and non-chemical treatment such as ultraviolet (UV) radiation. More particularly, the disinfection module 482 may utilize UV radiation having a particular wavelength and a power level selected based on the types of biological substances (e.g. pathogens) that pass through the upstream filters (e.g. filters 430a, 430b, 431a, 431b, or 431c). For example, the upstream filters may be ULPA filters that are 99.999% effective at removing contaminates larger than 120 nanometers, and the disinfection module 482 may apply radiation at a wavelength and power level so as to be 99.9% effective at eliminating biological substances smaller than 120 nanometers. As an example, the disinfection module may apply UV-C radiation in the range of about 240-280 nanometers and at a power level above about 30,000 microwatts-second per square centimeter (μw-s/cm^2), for example, using a low-pressure mercury vapour lamp that produces UV radiation at a wavelength of 254 nanometers.

The disinfection module 482 may also include a UV intensity monitor, for example, to indicate when UV lamps need to be changed.

As shown in FIGS. 11 and 12, the UV radiation disinfection module 482 is located downstream of one or more filters (e.g. e.g. filters 430a, 430b, 431a, 431b, or 431c), which may improve the effectiveness of the UV radiation disinfection module 482. In particular, the upstream filters may remove larger contaminates, which might otherwise shield UV radiation and prevent the radiation from eliminating smaller biological substances.

In some embodiments, the disinfection module 482 may use other disinfection techniques, such as other forms of radiation (e.g. gamma radiation), heat disinfection, and/or chemical treatment (e.g. ozone, chlorine, or hydrogen peroxide).

As shown in FIG. 12, the disinfection module 482 is located downstream of the condenser 480. As such, the disinfection module 482 receives a dehumidified exhaust gas from the condenser 480. Accordingly, the condenser 480 can remove a substantial amount of moisture prior to disinfecting the exhaust gas, which may increase the efficiency or effectiveness of the disinfection module 482. For example, some life forms travel in moisture, and it might be possible to remove some of these life forms by extracting moisture from the exhaust gases. Once the moisture has been extracted, the disinfection module 482 may have fewer life forms to eliminate.

In other embodiments, the condenser 480 may be located downstream of the disinfection module 482. This configuration offers the ability to disinfect the exhaust gas flow prior to condensation, which may be desirable, for example, where regulations require treatment of any extracted moisture prior to being discharged to a sewage system (e.g. via the drain 481).

In some embodiments, the subsystem 402 may include another disinfection module located on the drain 481, which may be configured specifically for water treatment so as to reduce or eliminate contaminates flowing down the drain 481.

While some exemplary locations for the condenser 480 and disinfection module 482 have been described, the condenser 480 and disinfection module 482 may have other locations within the subsystem. For example, the condenser 480 and disinfection module 482 may be located within the operating room 412, which may allow disinfection/sterilization of exhaust gases during localized collection of anaesthetic agents (e.g. without a centralized collection system).

Another difference between the subsystem 402 and the subsystem 302 is that the collection system 410 includes a dryer regeneration module 490 for regenerating the dryer 440 (e.g. when the dryer includes desiccant that is full of moisture). For example, the dryer regeneration module 490 may supply dry air to purge moisture from the dryer 440 and vent the moisture through an exhaust (e.g. via piping 441). As shown, the dryer regeneration module 490 may include a heated blower purge module 490a (which may be the same as or similar to the dryer regeneration module 60). The dryer regeneration module 490 may also include a regeneration dryer 490b for removing moisture from the main dryer 440 as described below.

The regeneration dryer 490b may include a twin tower desiccant dryer having a first desiccant tower 491a, a second desiccant tower 491b, and a compressor 491c for blowing air from the regeneration dryer 490 through the main dryer 440. Each of the desiccant towers 491a and 491b is selectively operable in a drying mode for regenerating the main dryer 440, or a purging mode so as to purge moisture from the desiccant tower.

In operation, the compressor pulls outside air through a first desiccant tower 491a, which is operating in drying mode so as to remove moisture from the outside air. The compressor then blows the dehumidified outside air (e.g. purging air) through the main dryer 440 so as to regenerate the desiccant therein. While the first desiccant tower 491a is in drying mode, the second desiccant tower 491b is in purge mode such that a portion of the dehumidified purging air exiting the first desiccant tower 491a flows through the second desiccant tower 491b so as to purge moisture from the second desiccant tower 491b.

When the first desiccant tower 491a is full of moisture, the operation switches so that the second desiccant tower 491b operates in drying mode while the first desiccant tower 491a operates in purge mode. As such, the twin tower desiccant dryer allows continuous purging of the main dryer 440, even when one desiccant tower is saturated with moisture. The system may include control valves for controlling when the desiccant towers 491a and 491b are in drying mode and purge mode.

The main dryer 440 may also include a plurality of dryers fluidly coupled in parallel (e.g. similar to the twin tower desiccant dryer of the regeneration dryer 490b). For example, a first dryer (e.g. a first desiccant tower 440a) may remove moisture from the exhaust gases while the regeneration module 490 (e.g. the regeneration dryer 490b) regenerates or purges moisture from a second dryer (e.g. a second desiccant tower 440b).

Then, when the first desiccant tower 440a is saturated with moisture, the operation may switch such that the regeneration module 490 begins regenerating the first desiccant tower 440a while the second desiccant tower 440b removes moisture from the exhaust gases. The system may include control valves for controlling when the two desiccant towers 440a and 440b are in operation (i.e. removing moisture from the exhaust gases) or being purged by the regeneration module 490.

In some embodiments, air supplied from the regeneration module 490 (e.g. the regeneration dryer 490b) may also be used to operate one or more pneumatically controlled valves within the system (e.g. valves 50, 70, 72, 84, 86, 88 described previously with respect to the collection system 10). More particularly, the compressor 491c of the regeneration dryer 490b may supply pressurized air for operating the control valves.

The collection system 410 may also include a bank of filters (e.g. filters 492a and 492b) between the dryer 440 and the collectors 442. This bank of filters offers another opportunity to remove contaminants and other particulates from the exhaust gases prior to entering the collectors 442. For example, the filters 492a and 492b may remove particulates such as desiccant particles entrained in the exhaust gases after passing through the dryer 440. The filters 492a and 492b might also remove biological substances that remain in the exhaust gases after being treated by the disinfection module 482. In particular, the filters 492a and 492b may filter out microorganisms that were killed by the disinfection module 482.

In some embodiments, the filters 492a and 492b may be located in other positions, for example, upstream of the oxygen collector 460 or upstream of the dryer 440.

Figure 13:
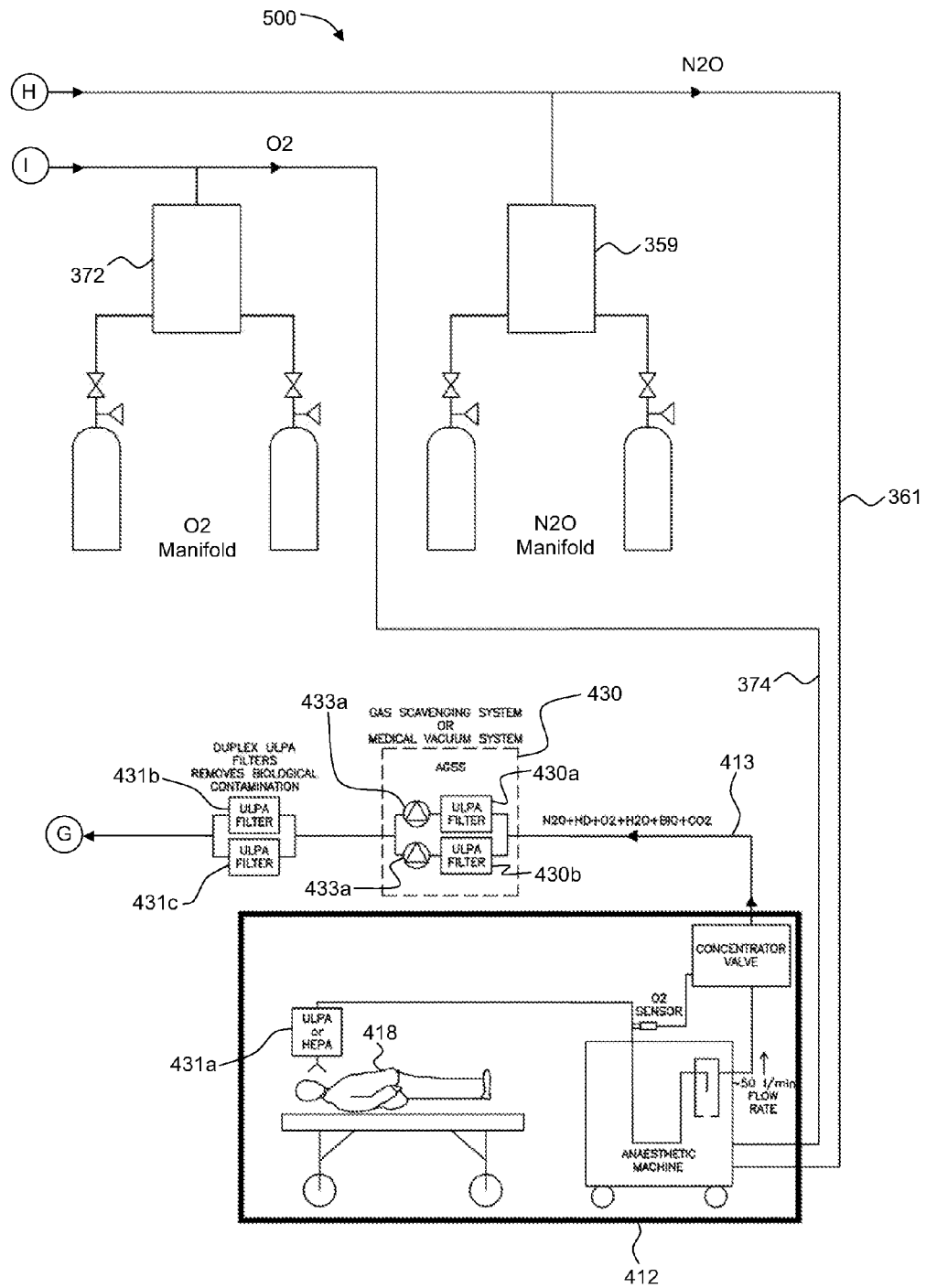
FIG. 13 is a schematic representation of a first subsystem of a yet another collection system for collecting anaesthetic agents.
Figure 14:
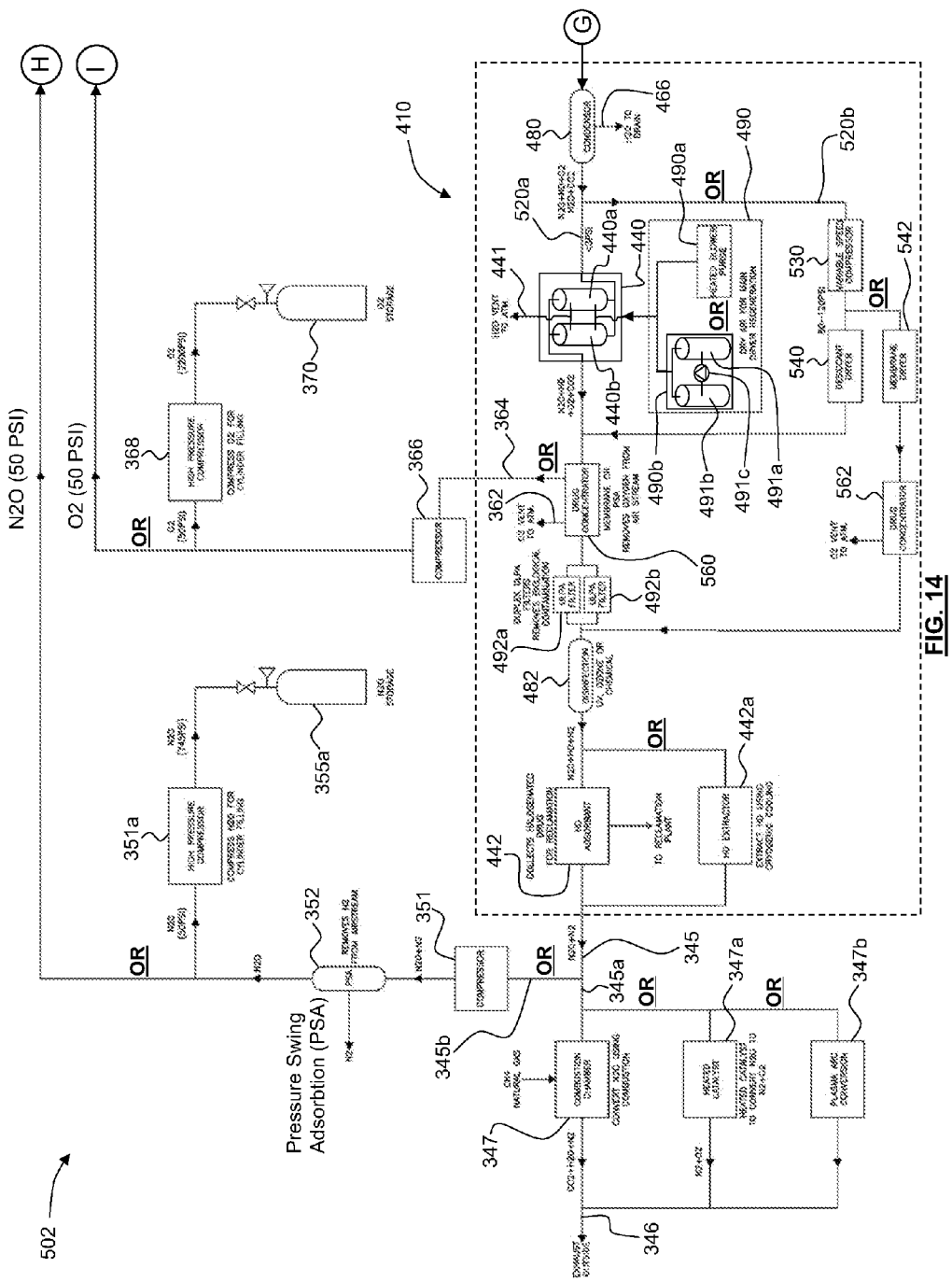
FIG. 14 a schematic representation of another subsystem for use with the first subsystem of FIG. 13, and which is operable to disinfect exhaust gases prior to collecting the anaesthetic agents.

Referring now to FIGS. 13 and 14, illustrated therein is another system for collecting anaesthetic agents, including a first subsystem 500 and a second subsystem 502.

Referring to FIG. 13, the first subsystem 500 is similar in many respects to the first subsystem 400 shown in FIG. 11. One difference is that the filters 431b and 431c are located downstream of the AGSS 430. Positioning the filters after the AGSS 430 may increase filtration efficiency, for example, because the exhaust gases leaving the AGSS 430 are under positive pressure, and the filters may be more efficient when filtering exhaust gases under positive pressure (e.g. approximately 3 psi) as opposed filtration under negative pressure upstream of the AGSS (e.g. 12-20 inches-Hg).

Another difference is that the subsystem 500 identifies carbon dioxide (CO2) as a substance within the exhaust gases. It will be understood that previous embodiments may also include carbon dioxide within the exhaust gases even if not expressly identified.

Referring now to FIG. 14, the second subsystem 502 is similar in many respects to the second subsystem 402 shown in FIG. 12. One difference is that the disinfection module 482 is located further downstream within the collection system 410 (i.e. between the filters 492a and 492b and the collectors 442). Positioning the disinfection module 482 further downstream may increase the effectiveness of the disinfection module 482, for example, because other system components might remove substances that would otherwise interfere with the disinfection process. In particular, particles such as water molecules might block UV radiation that is used to disinfect the exhaust gases. Accordingly, it might be desirable to remove these substances (e.g. using dryers, filters, membrane separators and the like) prior to disinfecting the exhaust gas.

Another difference is that the second subsystem 502 includes a number of devices and processes for drying the exhaust gases prior to collection. For example, as described previously with respect to FIG. 12, at least some of the exhaust gases may be fed to the dryer 440 (e.g. via piping 520a) for removing moisture.

Furthermore, in some embodiments, at least some of the exhaust gases may be fed to a compressor 530 (e.g. via piping 520b) for increasing the pressure of the exhaust gases. For example, the compressor 530 may receive the exhaust gases at a low pressure (e.g. at approximately 3 psi) and may output the exhaust gases at a high pressure (e.g. at approximately 80-120 psi). The compressor 530 may be a variable speed compressor (e.g. as shown in FIG. 14) or another type of compressor such as a fixed speed compressor.

The high pressure exhaust gases leaving the compressor 530 may be fed to one or more dryers. For example, at least some of the high pressure exhaust gases may be fed to a desiccant dryer 540 (e.g. similar to the dryers 40, 340, and 440). The dryer 540 may be more efficient at removing moisture from high pressure exhaust gases in comparison to low pressure exhaust gases, for example, because the flow rate of the exhaust gases through the dryer 540 can be increased, or because the size of the dryer 540 can be reduced, or both.

Furthermore, at least some of the high pressure exhaust gases leaving the compressor 530 may be fed to a membrane dryer 542. The membrane dryer 542 generally includes a porous membrane separator that removes water vapor from the high pressure exhaust gases, for example, based on selective adsorption of water molecules. Similar to the desiccant dryer 540, the membrane dryer 542 may be more efficient at removing moisture from high pressure exhaust gases in comparison to low pressure exhaust gases.

As shown, the portion of the exhaust gases leaving the dryer 440 and the desiccant dryer 540 may pass through a drug concentrator 560 and then through a set of filters 492a and 492b. The filters 492a and 492b may filter out desiccant particles that may be entrained in the exhaust gases after passing through the dryers 440 and 540.

The drug concentrator 560 may remove substances from the exhaust gases (e.g. oxygen, carbon dioxide and the like) so as to increase the concentration of anaesthetic agents prior to collection using the collectors 442. In some embodiments, the drug concentrator 560 may include an adsorbent material, a membrane separator (e.g. similar to the oxygen collector 360), or a PSA module. The substances collected by the drug concentrator 560 may be vented to atmosphere (e.g. via piping 462), or may be collected for subsequent use (e.g. oxygen may be routed to the compressor 366 via piping 364 for storage in the storage tank 370, or for resupply to patients via the oxygen manifold 372).

While FIG. 14 refers to a few specific examples of drug concentrators, the drug concentrator 560 is more generally any device that removes a substance from the exhaust gas prior to collection of the anaesthetic agents (e.g. to increase the concentration of the anaesthetic agent within the exhaust gas). Accordingly, in some embodiments, the drug concentrator 560 may include filters (e.g. filters 430a, 430b, 431a, 431b, 431c, 492a, 492b, etc), dryers (e.g. dryers 440, 540, 542, or the condenser 480), membrane separators, PSA modules, and the like.

Similar to the exhaust gases leaving the dryer 440 and the desiccant dryer 540, the portion of the exhaust gases leaving the member dryer 542 may also flow through a drug concentrator 562, which may be the same as, or similar to, the drug concentrator 560. In some embodiments, the membrane dryer 542 and the drug concentrator 562 may be incorporated into a single membrane separator that removes both water molecules and other gases such as oxygen and carbon dioxide.

While the exhaust gases leaving the membrane dryer 542 pass through a drug concentrator, it can be seen that these exhaust gases do not pass through any additional filters (e.g. like the filters 492a and 492b). The filters may be omitted, for example, because the membrane dryer 542 does not use desiccant particles that might otherwise contaminate the exhaust gases (whereas the dryers 440 and 540 might introduce desiccant particles and it might be desirable to filter out those desiccant particles).

In some embodiments, the condenser 480 may be located after the compressor 530, which may increase the efficiency of the condenser 480. For example, the condenser 480 may be more efficient at removing moisture from high pressure exhaust gases (approximately 80-120 psi) in comparison to low pressure exhaust gases (e.g. approximately 3 psi) because the water vapor in the high pressure exhaust gases has a higher condensation temperature (i.e. a higher dew point). A higher condensation temperature allows the condenser 480 to operate at a higher temperature (e.g. without the need to refrigerate the exhaust gases), which may increase the efficiency of the condenser 480.

Another difference between the subsystem 502 and the subsystem 402 is that the gas products exhausted by the collectors 442 may be sent via piping 345a to another type of reaction chamber 347b for decomposing nitrous oxide within the gas products. In particular, the reaction chamber 347b may include a plasma arc conversion module that feeds the gas products through a high temperature plasma torch so as to decompose the nitrous oxide into nitrogen and oxygen.

While some of the embodiments described above may refer to collecting or reclaiming halogenated drugs, the apparatus, systems and methods described herein may generally be used for the collection of various types of anaesthetic agents, including halogenated drugs and other agents.

Although the above description provides examples of one or more methods, systems and apparatuses, it will be appreciated that other methods, systems and apparatuses may be within the scope of the present description as interpreted by one of skill in the art.

The invention claimed is:

1. A conservation valve for use with a collection system for collecting an anaesthetic agent, the conservation valve comprising:
    a valve body having an inlet port, an outlet port, and a fluid passageway between the inlet port and the outlet port, the inlet port connectable to a source of exhaust gas so as to allow the exhaust gas to flow through the fluid passageway, and the outlet port connectable to the collection system;
    a sensor located upstream of the valve body for detecting a percentage content of at least one particular compound within the exhaust gas, the percentage content of the at least one particular compound being indicative of the anaesthetic agent being present or absent within the exhaust gas;
    an actuator located downstream of the sensor for selectively opening and closing the fluid passageway; and
    a processor for operating the actuator, the processor configured to:
        open the fluid passageway when the percentage content of the at least one particular compound is within a particular range indicative of the anaesthetic agent being present to allow the collection system to collect the anaesthetic agent;
        close the fluid passageway when the percentage content of the at least one particular compound is beyond the particular range indicative of the anaesthetic agent being absent to isolate the exhaust gas from the collection system, and
        keep the fluid passageway open for a particular waiting period before closing the fluid passageway, wherein the particular waiting period is greater than one minute.

2. The conservation valve of claim 1, wherein the sensor is an oxygen sensor for measuring an oxygen content within the exhaust gas.

3. The conservation valve of claim 2, wherein the actuator opens the fluid passageway when the measured oxygen content is outside the particular range, and wherein the particular range is between 19% and 23% oxygen.

4. The conservation valve of claim 1, wherein the percentage content of the at least one particular compound is calculated as an average over a particular time interval.

5. The conservation valve of claim 4, wherein the particular time interval is between ten seconds and five minutes.

6. The conservation valve of claim 1, wherein the particular waiting period is less than one hour.

7. The conservation valve of claim 1, wherein the at least one particular compound includes the anaesthetic agent.

8. A method of using a conservation valve to operate a collection system for collecting an anaesthetic agent, the conservation valve including: a valve body having an inlet port connected to a source of exhaust gas, an outlet port connected to the collection system, and a fluid passageway between the inlet port and the outlet port; a sensor located upstream of the valve body; an actuator located downstream of the sensor; and a processor for operating the actuator; the method comprising:
    receiving a flow of the exhaust gas from the source of the exhaust gas;
    detecting a percentage content of at least one particular compound within the exhaust gas using the sensor located upstream of the valve body, the percentage content of the at least one particular compound being indicative of the anaesthetic agent being present or absent within the exhaust gas; and
    selectively opening and closing the fluid passageway by using the processor to operate the actuator located downstream of the sensor, the actuator being operated by the processor to:
        open the fluid passageway when the percentage content of the at least one particular compound is indicative of the anaesthetic agent being present so as to allow the collection system to collect the anaesthetic agent; and
        close the fluid passageway when the percentage content of the at least one particular compound is indicative of the anaesthetic agent being absent so as to isolate the exhaust gas from the collection system, and
        keep the fluid passageway open for a particular waiting period before closing the fluid passageway, wherein the particular waiting period is greater than one minute.

9. The method of claim 8, wherein the detecting step includes measuring an oxygen content within the exhaust gas.

10. The method of claim 9, wherein the actuator is operated by the processor to open the fluid passageway when the measured oxygen content is outside a particular range.

11. The method of claim 10, and wherein the particular range is between 19% and 23% oxygen.

12. The method of claim 8, wherein the actuator is operated by the processor to open and close the fluid passageway based on whether the percentage content of the at least one particular compound falls within a particular range.

13. The method of claim 8, wherein the processor calculates the percentage content of the at least one particular compound as an average over a particular time interval.

14. The method of claim 13, wherein the particular time interval is between ten seconds and five minutes.

15. The method of claim 8, wherein the particular waiting period is less than one hour.

16. The method of claim 8, further comprising operating at least one anaesthetic gas scavenging system (AGSS) connected to the outlet port of the valve body, the at least one AGSS comprises at least one power source for providing suction of the exhaust gas from the source of the exhaust gas, the AGSS being operated to:
    turn on the power source when the fluid passageway is open so as to provide suction of the exhaust gas; and
    turn off the power source when the fluid passageway is closed.

17. The method of claim 8, wherein the at least one particular compound includes the anaesthetic agent.

* * * * *